US010609956B2

(12) United States Patent
Takeuchi et al.

(10) Patent No.: US 10,609,956 B2
(45) Date of Patent: Apr. 7, 2020

(54) NON-BURNING-TYPE FLAVOR INHALER

(71) Applicant: JAPAN TOBACCO INC., Tokyo (JP)

(72) Inventors: Manabu Takeuchi, Tokyo (JP);
Takuma Nakano, Tokyo (JP); Manabu Yamada, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 490 days.

(21) Appl. No.: 15/340,054

(22) Filed: Nov. 1, 2016

(65) Prior Publication Data

US 2017/0042250 A1 Feb. 16, 2017

Related U.S. Application Data

(63) Continuation of application No. PCT/JP2015/063040, filed on Apr. 30, 2015.

(30) Foreign Application Priority Data

May 2, 2014 (JP) .................................. 2014-095164

(51) Int. Cl.
*A24F 47/00* (2020.01)
*A61M 15/06* (2006.01)
(Continued)

(52) U.S. Cl.
CPC .............. *A24F 47/008* (2013.01); *A24F 7/02* (2013.01); *A24F 47/00* (2013.01); *A61M 11/042* (2014.02);
(Continued)

(58) Field of Classification Search
CPC .... A24F 47/002; A24F 47/004; A24F 47/008; A24F 47/00; A24F 7/02; A61M 15/06;
(Continued)

(56) References Cited

U.S. PATENT DOCUMENTS 5,134,886 A  8/1992 Ball
2008/0092912 A1  4/2008 Robinson et al.
(Continued)

FOREIGN PATENT DOCUMENTS

CN  102227175 A  10/2011
CN  102264420 A  11/2011
(Continued)

OTHER PUBLICATIONS

Extended European Search Report for European Application No. 15785600.6, dated Dec. 20, 2017.
(Continued)

*Primary Examiner* — Michael H. Wilson
*Assistant Examiner* — Yana B Krinker
(74) *Attorney, Agent, or Firm* — Birch, Stewart, Kolasch & Birch, LLP

(57) ABSTRACT

A non-burning type flavor inhaler, comprises: a housing having an airflow path that continues from an inlet to an outlet; an atomizer configured to atomize an aerosol source without burning; a sensor including a capacitor, the sensor outputting a value indicating electric capacitance of the capacitor, the electric capacitance changed depending on a puff action of a user; and a controller configured to detect a start or an end of a puff duration on the basis of an output value that is output from the sensor. The controller detects the start or the end of the puff duration when an inclination formed by two or more of the output values has a predetermined sign and when an absolute value of the inclination having the predetermined sign is larger than a predetermined value.

7 Claims, 12 Drawing Sheets

(51) Int. Cl.
*A61M 11/04* (2006.01)
*A24F 7/02* (2006.01)
*H05B 1/02* (2006.01)

(52) U.S. Cl.
CPC ........... *A61M 15/06* (2013.01); *H05B 1/0244* (2013.01); *A61M 2205/27* (2013.01); *A61M 2205/3653* (2013.01); *A61M 2205/50* (2013.01); *A61M 2205/587* (2013.01); *A61M 2205/60* (2013.01); *A61M 2205/8206* (2013.01); *H05B 2203/021* (2013.01)

(58) Field of Classification Search
CPC ........... A61M 11/042; A61M 2205/27; A61M 2205/3653; A61M 2205/50; A61M 2205/587; A61M 2205/60; A61M 2205/8206; H05B 1/0244; H05B 2203/021
See application file for complete search history.

(56) References Cited

U.S. PATENT DOCUMENTS

| | | |
|---|---|---|
| 2011/0226236 A1 | 9/2011 | Buchberger |
| 2012/0186594 A1 | 7/2012 | Liu |
| 2012/0199146 A1* | 8/2012 | Marangos ............. A24F 47/008 131/328 |
| 2013/0284192 A1 | 10/2013 | Peleg et al. |
| 2013/0319439 A1 | 12/2013 | Gorelick et al. |

FOREIGN PATENT DOCUMENTS

| | | | | |
|---|---|---|---|---|
| CN | 103948177 A | 7/2014 | | |
| EP | 2460423 A1 | 6/2012 | | |
| JP | H07-124259 A | 5/1995 | | |
| JP | 2010-506594 A | 3/2010 | | |
| JP | 2013-526834 A | 6/2013 | | |
| WO | WO 2012/072790 A1 | 6/2012 | | |
| WO | WO-2013016846 A1 * | 2/2013 | ............ H04R 1/028 |
| WO | WO 2013/034456 A1 | 3/2013 | | |
| WO | WO 2013/060784 A2 | 5/2013 | | |
| WO | WO 2014/037259 A1 | 3/2014 | | |
| WO | WO 2014/054035 A1 | 4/2014 | | |
| WO | WO 2014/058678 A1 | 4/2014 | | |
| WO | WO 2014/150704 A2 | 9/2014 | | |

OTHER PUBLICATIONS

Extended European Search Report for European Application No. 15785768.1, dated Dec. 20, 2017.
International Search Report for PCT/JP2015/063040 (PCT/ISA/210) dated Jul. 21, 2015.
International Search Report for for PCT/JP2015/063036 (PCT/ISA/210) dated Aug. 4, 2015.

* cited by examiner

FIG. 6

| PUFFING STATE | NON-PUFFING STATE #1 | PUFFING STATE #1 | NON-PUFFING STATE #2 | PUFFING STATE #2 | NON-PUFFING STATE #3 | PUFFING STATE #3 | NON-PUFFING STATE #4 | PUFFING STATE #4 |
|---|---|---|---|---|---|---|---|---|
| LIGHT-EMITTING MODE | LIGHT-EMITTING MODE #2-1 | LIGHT-EMITTING MODE #1 | LIGHT-EMITTING MODE #2-1 | LIGHT-EMITTING MODE #1 | LIGHT-EMITTING MODE #2-1 | LIGHT-EMITTING MODE #1 | LIGHT-EMITTING MODE #2-1 | LIGHT-EMITTING MODE #1 |

| PUFFING STATE | NON-PUFFING STATE #5 | PUFFING STATE #5 | NON-PUFFING STATE #6 | PUFFING STATE #6 | NON-PUFFING STATE #7 | PUFFING STATE #7 | NON-PUFFING STATE #8 | PUFFING STATE #8 | NON-PUFFING STATE #9 AND THEREAFTER | PUFFING STATE #9 AND THEREAFTER |
|---|---|---|---|---|---|---|---|---|---|---|
| LIGHT-EMITTING MODE | LIGHT-EMITTING MODE #2-2 | LIGHT-EMITTING MODE #1 | LIGHT-EMITTING MODE #2-2 | LIGHT-EMITTING MODE #1 | LIGHT-EMITTING MODE #2-2 | LIGHT-EMITTING MODE #1 | LIGHT-EMITTING MODE #2-3 | LIGHT-EMITTING MODE #1 | END LIGHT-EMITTING MODE | LIGHT-EMITTING MODE #1 |

FIG. 7

| PUFFING STATE | NON-PUFFING STATE #1 | PUFFING STATE #1 | NON-PUFFING STATE #2 | PUFFING STATE #2 | NON-PUFFING STATE #3 | PUFFING STATE #3 | NON-PUFFING STATE #4 | PUFFING STATE #4 |
|---|---|---|---|---|---|---|---|---|
| LIGHT-EMITTING MODE | LIGHT-EMITTING MODE #2-1 | LIGHT-EMITTING MODE #1-1 | LIGHT-EMITTING MODE #2-1 | LIGHT-EMITTING MODE #1-1 | LIGHT-EMITTING MODE #2-1 | LIGHT-EMITTING MODE #1-1 | LIGHT-EMITTING MODE #2-1 | LIGHT-EMITTING MODE #1-1 |

| PUFFING STATE | NON-PUFFING STATE #5 | PUFFING STATE #5 | NON-PUFFING STATE #6 | PUFFING STATE #6 | NON-PUFFING STATE #7 | PUFFING STATE #7 | NON-PUFFING STATE #8 | PUFFING STATE #8 | NON-PUFFING STATE #9 AND THEREAFTER | PUFFING STATE #9 AND THEREAFTER |
|---|---|---|---|---|---|---|---|---|---|---|
| LIGHT-EMITTING MODE | LIGHT-EMITTING MODE #2-2 | LIGHT-EMITTING MODE #1-2 | LIGHT-EMITTING MODE #2-2 | LIGHT-EMITTING MODE #1-2 | LIGHT-EMITTING MODE #2-2 | LIGHT-EMITTING MODE #1-2 | LIGHT-EMITTING MODE #2-3 | LIGHT-EMITTING MODE #1-3 | END LIGHT-EMITTING MODE | LIGHT-EMITTING MODE #1-4 |

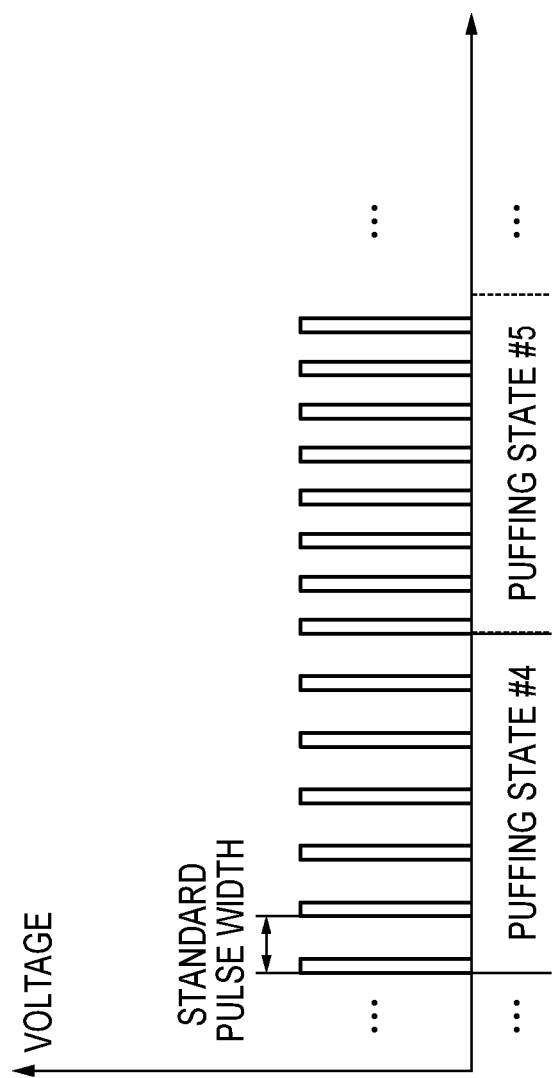

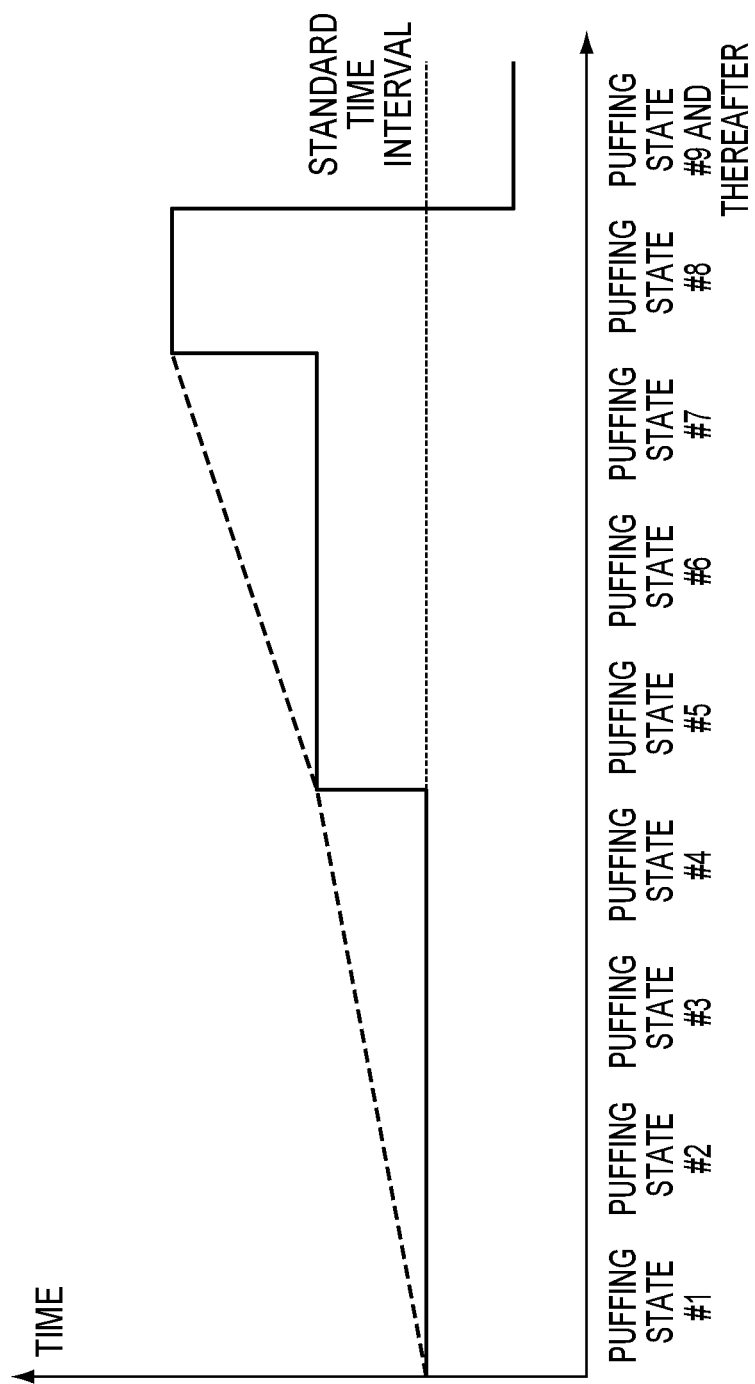

NON-BURNING-TYPE FLAVOR INHALER

CROSS REFERENCE TO RELATED APPLICATIONS:

This application is a Continuation of PCT International Application No. PCT/JP2015/063040, filed on Apr. 30, 2015, which claims priority under 35 U.S.C. 119(a) to Patent Application No. 2014-095164, filed in Japan on May 2, 2014, all of which are hereby expressly incorporated by reference into the present application.

TECHNICAL FIELD

The present invention relates to a non-burning type flavor inhaler having an atomizer configured to atomize an aerosol source without burning.

BACKGROUND ART

Conventionally, there is known a non-burning type flavor inhaler for inhaling flavor without burning. The non-burning type flavor inhaler has an atomizer configured to atomize an aerosol source without burning.

With such a non-burning type flavor inhaler, power source output is supplied to the atomizer in a puff duration during which a puff action is performed, and power source output is not supplied to the atomizer in a non-puff duration during which the puff action is not performed. That is, the above-described non-burning type flavor inhaler requires at least sensor for detecting a puff duration. As such a sensor, it is possible to use a sensor configured to output a value changed depending on the puff action (for example, Patent Documents 1 and 2).

PRIOR ART DOCUMENT

Patent Document

Patent Document 1: JP 2010-506594 A
Patent Document 2: WO 2012/072790 A1

SUMMARY

A first feature is summarized as a non-burning type flavor inhaler, comprising: a housing having an airflow path that continues from an inlet to an outlet; an atomizer configured to atomize an aerosol source without burning; a sensor including a capacitor, the sensor outputting a value indicating electric capacitance of the capacitor, the electric capacitance changed depending on a puff action of a user; and a controller configured to detect a start or an end of a puff duration on the basis of an output value that is output from the sensor, wherein the controller detects the start or the end of the puff duration when an inclination formed by two or more of the output values has a predetermined sign and when an absolute value of the inclination having the predetermined sign is larger than a predetermined value.

A second feature according to the first feature is summarized as that a cycle for monitoring the output value output from the sensor before detecting the start of the puff duration is shorter than a cycle for monitoring the output value output from the sensor after detecting the start of the puff duration, and a cycle for monitoring the output value output from the sensor after detecting the end of the puff duration is shorter than a cycle for monitoring the output value output from the sensor before detecting the end of the puff duration.

A third feature according to the first feature or the second feature is summarized as that $\Delta t$ represents a cycle for monitoring the output value output from the sensor, $D(n)$ represents the output value output from the sensor at a time $t(n)$, $\alpha(n)$ represents a positive integer, $S(n)$ represents an inclination formed by the output value output from the sensor at a time $t(n)$, the controller calculates the inclination formed by the output value output from the sensor based on $S(n)=\{D(n)-D(n-\alpha(n)\times\Delta t)\}/(\alpha(n)\times\Delta t)$, the controller detects the start or the end of the puff duration when a condition in that $S(n)$ is a value of the predetermined sign and an absolute value of $S(n)$ is larger than a first value is satisfied for consecutive m times (m is an integer of 2 or more) of $S(n)$.

A fourth feature according to the third feature is summarized as that a sampling cycle of the output value that is referenced upon detecting the start or the end of the puff duration is longer than a predetermined time, and the predetermined time is longer than ½ of an average value of wavelength of the output value varied in the puff duration.

A fifth feature according to the third feature or the fourth feature is summarized as that the controller detects the start or the end of the puff duration when a condition that $S(n)$ is a value of the predetermined sign and an absolute value of $S(n)$ is smaller than a second value is satisfied for one time of the consecutive m times of $S(n)$, and the second value is an average value of an absolute value of the inclination formed by the output value varied in the puff duration.

A sixth feature according to any one of the first feature to the fifth feature is summarized as that the sensor is a capacitor microphone sensor.

A seventh feature according to any one of the first feature to the sixth feature is summarized as comprising a switch member used for starting and stopping a supply of power source output to the controller and the sensor.

BRIEF DESCRIPTION OF THE DRAWINGS

FIG. 6 is a diagram showing an example of a light emitting mode according to the first embodiment.

FIG. 7 is a diagram showing an example of the light emitting mode according to the first embodiment.

FIG. 12 is a diagram showing an example of power control in a puff action series according to a first modification of the first embodiment.

FIG. 13 is a diagram showing an example of power control in a puff action series according to a second modification of the first embodiment.

DESCRIPTION OF THE EMBODIMENT

Figure 1:
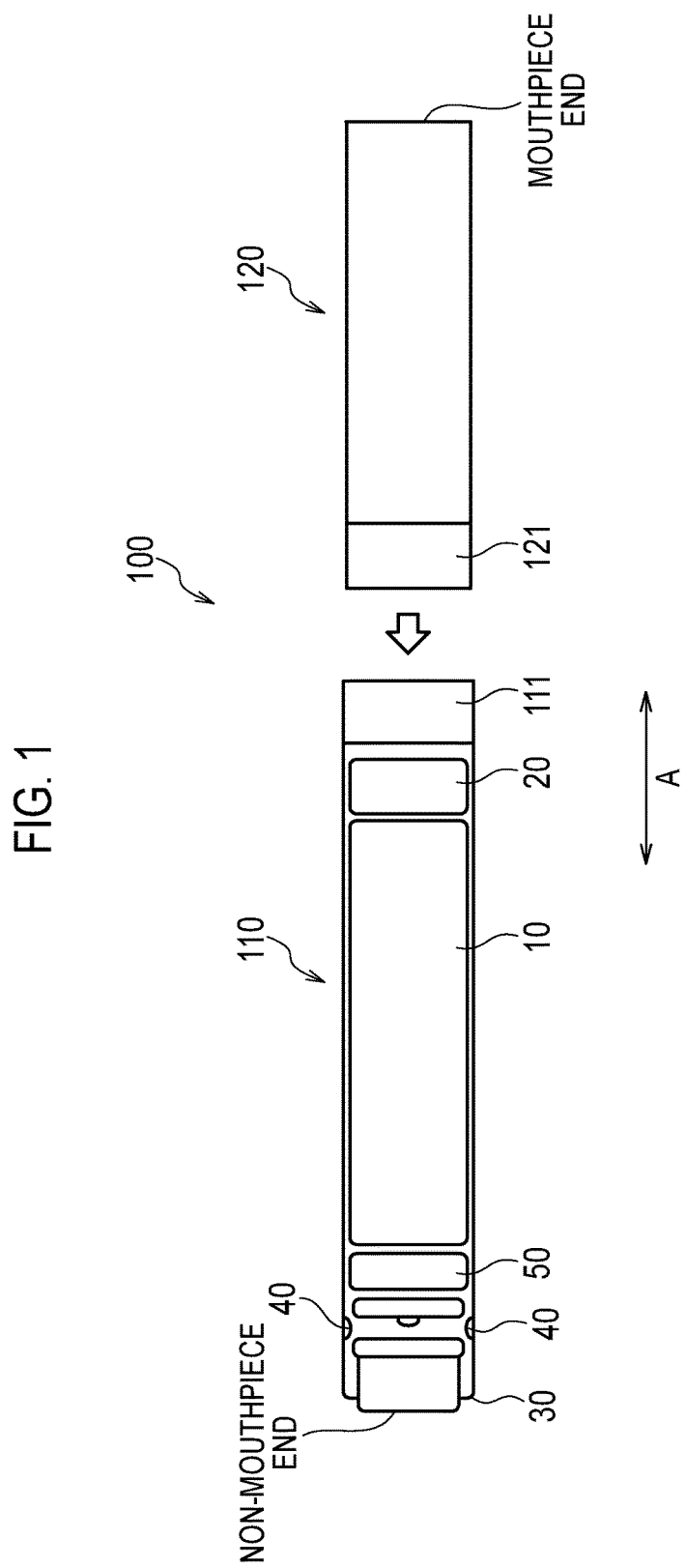
FIG. 1 is a diagram showing a non-burning type flavor inhaler 100 according to a first embodiment.

Hereinafter, the embodiments of the present invention will be described. In the following drawings, identical or similar components are denoted by identical or similar reference numerals. However, it should be noted that the drawings are schematic, and the ratio and the like of each of the dimensions is different from the reality.

Therefore, specific dimensions should be determined with reference to the description below. It is needless to mention that different relationships and ratio of dimensions may be included in different drawings.

[Overview of Embodiment]

With the non-burning type flavor inhaler mentioned in the background art, a puff duration is detected on the basis of an absolute value of a detection value that is output from a sensor. However, as a result of extensive studies, the inventors found that an erroneous detection of the puff duration occurs when only monitoring the absolute value of the detection value. For example, when detecting the start of the puff duration by comparing the absolute value of the detection value with a threshold value, if a low threshold value is set, then a response of detecting the start of the puff duration is improved but the erroneous detection is increased. On the other hand, if a high threshold value is set, then the erroneous detection is decreased but the response of detecting the start of the puff duration is deteriorated. That is, the above-described trade-off relation is inevitable.

The non-burning type flavor inhaler according to the embodiment includes: a housing having an airflow path that continues from an inlet to an outlet; an atomizer configured to atomize an aerosol source without burning; a sensor including a capacitor, where the sensor outputs a value indicating electric capacitance of the capacitor changed depending on a puff action of a user; and a controller configured to detect, on the basis of an output value that is output from the sensor, a start or an end of a puff duration, such that the controller detects the start or the end of the puff duration, when an inclination formed by two or more output values has a predetermined sign and an absolute value of the inclination having the predetermined sign is larger than a predetermined value.

In the embodiment, the controller detects the start or the end of the puff duration, when an inclination formed by two or more output values that are output from the sensor has a predetermined sign and an absolute value of the inclination having the predetermined sign is larger than a predetermined value. Therefore, it is possible to reduce the possibility of erroneously detecting, as the start of the puff duration, an output result of the sensor (for example, the pressure change at a high place, the vibration of human voice, etc.) that is originally not intended as the start of the puff duration, and the possibility of deterioration in the following capability of the power source output to a heat source 80, and thus, it is possible to enhance the detection accuracy of the puff duration. That is, it is possible to achieve both the improvement in the detection accuracy of the puff duration and the improvement in the following capacity of the power source output.

In the embodiment, when detecting the start or the end of the puff duration, a sensor is used, configured to output a value indicating electric capacitance of a capacitor changed depending on the puff action of the user. That is, by focusing on a point that the pressure change within a housing configured to form an airflow path is specific in an early period and an ending period of inhaling action, then using a sensor capable of outputting such pressure change, a response of detecting the puff duration is improved.

[First Embodiment]

(Non-burning Type Flavor Inhaler)

Figure 2:
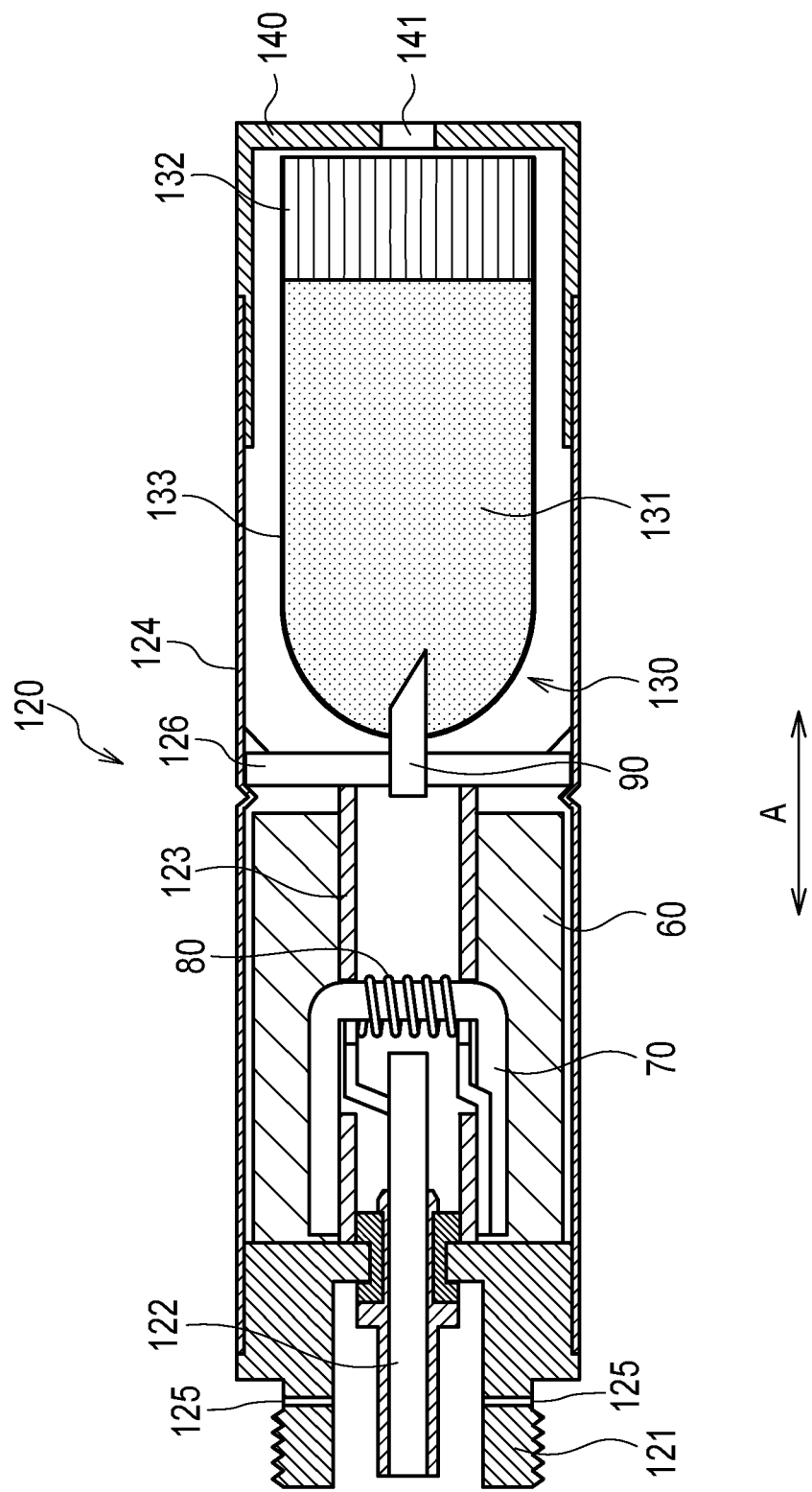
FIG. 2 is a diagram showing an atomization unit 120 according to the first embodiment.

A non-burning type flavor inhaler according to a first embodiment will be described, below. FIG. 1 is a diagram showing a non-burning type flavor inhaler 100 according to the first embodiment. FIG. 2 is a diagram showing an atomization unit 120 according to the first embodiment.

In the first embodiment, the non-burning type flavor inhaler 100 is a device for inhaling flavor without burning, and has a shape extending along a predetermined direction A from a non-mouthpiece side toward a mouthpiece side. In the first embodiment, the "mouthpiece side" may be considered synonymous with the "downstream" of the flow of the aerosol, and the "non-mouthpiece side" may be considered synonymous with the "upstream" of the flow of the aerosol.

As shown in FIG. 1, the non-burning type flavor inhaler 100 has an electrical unit 110 and an atomization unit 120. The electrical unit 110 has a female connector 111 at a site adjacent to the atomization unit 120, and the atomization unit 120 has a male connector 121 at a site adjacent to the electrical unit 110. The female connector 111 has a spiral groove extending along a direction perpendicular to the predetermined direction A, and the male connector 121 has a spiral projection extending along a direction perpendicular to the predetermined direction A. As a result of mating of the female connector 111 and the male connector 121, the atomization unit 120 and the electrical unit 110 are connected. The atomization unit 120 is configured in a removable manner with respect to the electrical unit 110.

The electrical unit 110 has a power source 10, a sensor 20, a push button 30, a light-emitting element 40, and a control circuit 50.

The power source 10 is, for example, a lithium ion battery. The power source 10 accumulates electric power necessary for the action of the non-burning type flavor inhaler 100. For example, the power source 10 accumulates electric power to be supplied to the sensor 20, the light-emitting element 40, and the control circuit 50. Further, the power source 10 accumulates electric power to be supplied to a heat source 80 described later.

The sensor 20 has a capacitor, and outputs a value indicating electric capacitance of the capacitor that changes in accordance with the air inhaled from the non-mouthpiece side toward the mouthpiece side (that is, the puff action of the user). Here, the value output by the sensor 20 is a voltage value. The sensor 20 is, for example, a capacitor microphone sensor.

Figure 3:
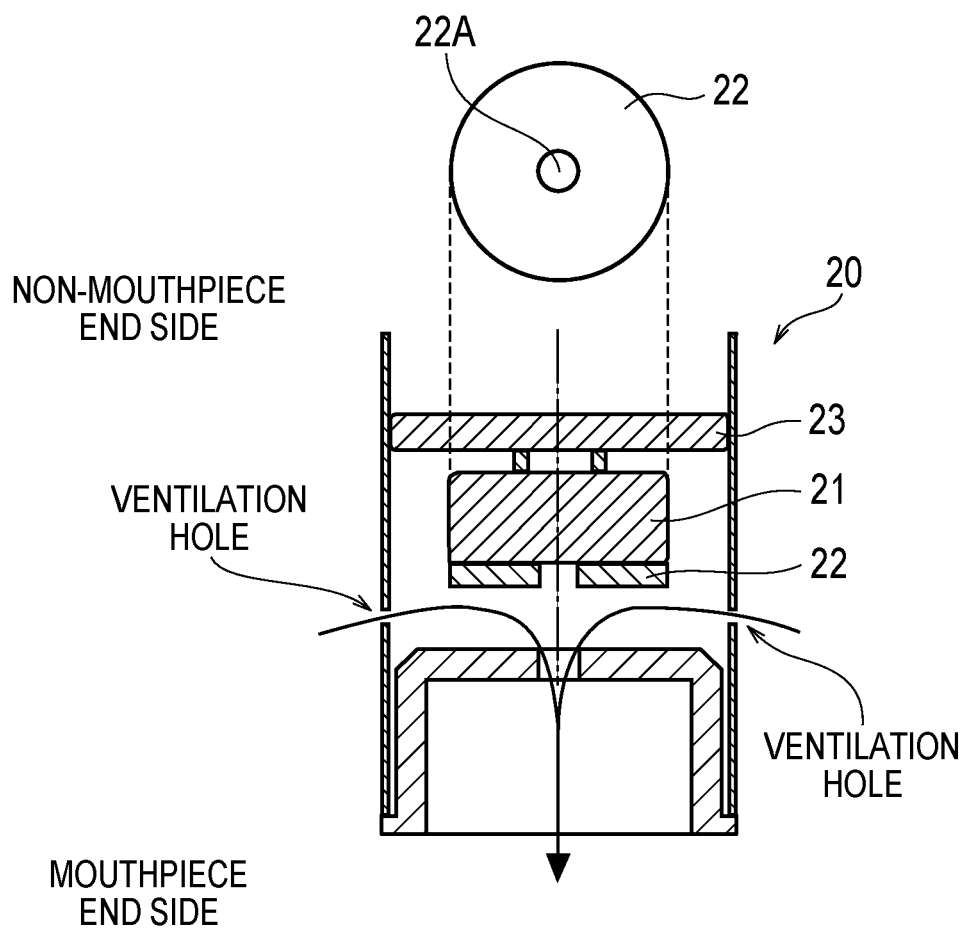
FIG. 3 is a diagram showing a sensor 20 according to the first embodiment.

Specifically, the sensor 20 has a sensor body 21, a cover 22, and a substrate 33, as shown in FIG. 3. The sensor body 21 is, for example, configured by a capacitor, and the electric capacitance of the sensor body 21 changes in accordance with the vibrations (pressure) generated by the air inhaled from an air lead-in hole 125 (that is, the air inhaled from the non-mouthpiece side toward the mouthpiece side). The cover 22 is provided at the mouthpiece side with respect to the sensor body 21, and has an opening 22A. By providing the cover 22 having the opening 22A, the electric capacitance of the sensor body 21 changes easily, and thereby the response characteristic of the sensor body 21 improves. The substrate 33 outputs a value (for example, a voltage value) indicating the electric capacitance of the sensor body 21.

It is noted that in FIG. 3, the cover 22 covers only the mouthpiece side end of the sensor body 21, but the first embodiment is not limited thereto. For example, in addition to the mouthpiece side end of the sensor body 21, the cover 22 may cover the side surface of the sensor body 21. FIG. 3 illustrates a case in which the air lead-in hole 125 is provided at the mouthpiece side from the sensor 20, but the first embodiment is not limited thereto. For example, the air lead-in hole 125 may be provided at the non-mouthpiece side from the sensor 20.

Referring back to FIG. 1, the push button 30 is configured to be pushed from the outer side of the non-burning type flavor inhaler 100 toward the inner side. In the first embodiment, the push button 30 is provided at the non-mouthpiece end of the non-burning type flavor inhaler 100, and is configured to be pushed in a direction from the non-mouthpiece end toward the mouthpiece end (that is, the predetermined direction A). For example, when the push button 30 is pushed continuously over a predetermined number of times, the power source of the non-burning type flavor inhaler 100 is turned ON. It is noted that the power source of the non-burning type flavor inhaler 100 may be disconnected when a predetermined time period elapses while a puff action is not being performed from the time a puff action is performed.

The light-emitting element 40 is, for example, a light source such as an LED or an electric lamp. The light-emitting element 40 is provided on a side wall extending along a predetermined direction. The light-emitting element 40 is preferably provided on a side wall near the non-mouthpiece end. As a result, as compared to a case in which the light-emitting element is provided only on an end face of the non-mouthpiece end on an axial line of the predetermined direction A, the user is capable of visually recognizing, during the puff action, a light-emitting pattern of the light-emitting element 40 with ease. The light-emitting pattern of the light-emitting element 40 is a pattern by which a condition of the non-burning type flavor inhaler 100 is notified to the user.

The control circuit 50 controls the action of the non-burning type flavor inhaler 100. Specifically, the control circuit 50 controls the light-emitting pattern of the light-emitting element 40, and controls the power source output to the heat source 80.

As shown in FIG. 2, the atomization unit 120 has a holder 60, an absorber 70, the heat source 80, and a destruction portion 90. The atomization unit 120 has a capsule unit 130 and a mouthpiece unit 140. Here, the atomization unit 120 has the air lead-in hole 125 for taking in the outside air, an air flow path 122 communicated to the electrical unit 110 (sensor 20) via the male connector 121, and a ceramic 123 arranged in a cylindrical shape. The atomization unit 120 has a cylindrical outer wall 124 configured to form the outer shape of the atomization unit 120. The space enclosed by the ceramic 123 forms an air flow path. The ceramic 123, for example, includes alumina as the main constituent.

The holder 60 has a cylindrical shape, and holds an aerosol source configured to generate aerosol. The aerosol source is a liquid, such as glycerine or propylene glycol. The holder 60 is configured by a porous body in which the aerosol source has been immersed, for example. The porous body is, for example, a resin web.

It is noted that in the first embodiment, the above-described ceramic 123 is arranged on the inner side of the holder 60, and the volatilization of the aerosol source held by the holder 60 is thus restrained.

The absorber 70 is provided adjacent to the holder 60, and is configured by a substance that sucks up the aerosol source from the holder 60. The absorber 70 is, for example, configured by a glass fiber.

The heat source 80 heats the aerosol source without burning. That is, the heat source 80 is an example of an atomizer configured to atomize atomizes an aerosol source without burning. For example, the heat source 80 is a heating wire wound around the absorber 70. The heat source 80 heats the aerosol source that is sucked up by the absorber 70.

In the first embodiment, a heating type component configured to atomize the aerosol source by heating is illustrated as the heat source 80. However, as long as the atomizer has a function of atomizing the aerosol source, the atomizer may be an ultrasonic wave type component configured to atomize the aerosol source by an ultrasonic wave.

The destruction portion 90 is a member for destructing a part of a predetermined film 133 in a state in which the capsule unit 130 has been mounted. In the embodiment, the destruction portion 90 is held by a partition member 126 for separating the atomization unit 120 and the capsule unit 130. The partition member 126 is, for example, a polyacetal resin. The destruction portion 90 is, for example, a tubular hollow needle extending along the predetermined direction A. By piercing the tip of the hollow needle through the predetermined film 133, a part of the predetermined film 133 is destructed. Further, an air flow path that pneumatically communicates the atomization unit 120 and the capsule unit 130 is formed by the inner space of the hollow needle. Here, a mesh that has a roughness of an extent such that the raw material configuring a tobacco source 131 does not pass through is preferably provided inside the hollow needle. The roughness of the mesh is, for example, 80 mesh or above and 200 mesh or below.

In such a case, the depth of penetration of the hollow needle inside the capsule unit 130 is preferably 1.0 mm or more and 5.0 mm or less, and more preferably 2.0 mm or more and 3.0 mm or less. As a result, since there is no destruction of sites other than the desired site of the predetermined film 133, it is possible to prevent the desorption of the tobacco source 131 that is packed in the space partitioned by the predetermined film 133 and a filter 132. Further, since the detachment of the hollow needle from the concerned space is prevented, it is possible to favorably maintain the appropriate air flow path extending from the hollow needle to the filter 132.

In the vertical cross-section with respect to the predetermined direction A, the cross-sectional area of the vertical needle is preferably 2.0 mm$^2$ or more and 3.0 mm$^2$ or less. As a result, it is possible to prevent the dropping out of the tobacco source 131 from the capsule unit 130 when the hollow needle is pulled out.

The tip of the hollow needle preferably has an inclination of 30° or more and 45° or less with respect to the vertical direction to the predetermined direction A.

However, the embodiment is not restricted thereto, and the destruction portion 90 may be a site adjacent to the predetermined film 133 in a state in which the capsule unit 130 has been mounted. Apart of the predetermined film 133 may thus be destructed through the application of pressure to such a site by the user.

The capsule unit 130 is configured in a removable manner with respect to a main body unit. The capsule unit 130 has the tobacco source 131, the filter 132, and the predetermined film 133. Further, the tobacco source 131 is packed in the space partitioned by the predetermined film 133 and the filter 132. Here, the main body unit is a unit configured by sites other than the capsule unit 130. For example, the main body unit includes the above-described electrical unit 110, the holder 60, the absorber 70, and the heat source 80.

The tobacco source 131 is provided at the mouthpiece side from the holder 60 configured to hold the aerosol source, and generates a flavor that is inhaled by the user together with the aerosol generated from the aerosol source. Here, it must be noted that the tobacco source 131 is configured by a solid substance so as not to flow out from inside the space partitioned by the predetermined film 133 and the filter 132. As the tobacco source 131, it is possible to use shredded tobacco, a formed product obtained by forming the tobacco raw material in the shape of granules, and a formed product obtained by forming the tobacco raw material in the shape of a sheet. Flavorings, such as menthol, etc. may be added to the tobacco source 131.

It is noted that when the tobacco source 131 is configured by the tobacco raw material, the tobacco raw material is away from the heat source 80, and therefore, is it possible to inhale the flavor without heating the tobacco raw material. In other words, it must be noted that inhalation of unnecessary substances generated by heating of the tobacco raw material is controlled.

In the first embodiment, the amount of the tobacco source 131 that is packed in the space partitioned by the filter 132 and the predetermined film 133 is preferably 0.15 g/cc or more and 1.00 g/cc or less. The occupancy rate of the volume occupied by the tobacco source 131 in the space partitioned by the filter 132 and the predetermined film 133 is preferably 50% or more and 100% or less. It is noted that the capacity of the space partitioned by the filter 132 and the predetermined film 133 is preferably 0.6 mL or more and 1.5 mL or less. As a result, it is possible to store the tobacco source 131 to an extent at which the user is capable of sufficiently tasting the flavor while retaining the capsule unit 130 at an appropriate size.

The air-flow resistance (pressure loss) of the capsule unit 130 in the case when air is inhaled at a flow rate of 1050 cc/min. from the tip portion (destructed portion) of the capsule unit 130 up to the end of the filter 132 in a state when a part of the predetermined film 133 is destructed by the destruction portion 90, and the atomization unit 120 and the capsule unit 130 are communicated is preferably 10 mmAq or more and 100 mmAq or less, and more preferably 20 mmAq or more and 90 mmAq or less, as a whole. By setting the air-flow resistance of the tobacco source 131 within the above-described preferred range, the phenomenon of over-filtration of the aerosol by the tobacco source 131 is controlled, and thus, it is possible to efficiently supply the flavor to the user. It is noted that since 1 mmAq is equivalent to 9.80665 Pa, the above-described air-flow resistance is possible to be expressed in Pa as well.

The filter 132 is adjacent to the mouthpiece side with respect to the tobacco source 131, and is configured by a substance having air permeability. The filter 132 is preferably, for example, an acetate filter. The filter 132 preferably has a roughness of an extent such that the raw material configuring the tobacco source 131 does not pass through.

The air-flow resistance of the filter 132 is preferably 5 mmAq or more and 20 mmAq or less. As a result, it is possible to efficiently let the aerosol pass through while efficiently adsorbing the vapor component generated from the tobacco source 131, and thus, it is possible to supply an appropriate flavor to the user. Further, it is possible to offer the user the appropriate sense of resistance to air.

The ratio (mass ratio) of the mass of the tobacco source 131 and the mass of the filter 132 is preferably in the range of 3:1 to 20:1, and more preferably in the range of 4:1 to 6:1.

The predetermined film 133 is integrally formed with the filter 132, and is configured by a member that does not have air permeability. Of the outer surface of the tobacco source 131, the predetermined film 133 covers a portion excluding the portion adjacent to the filter 132. The predetermined film 133 includes at least one compound selected from a group configured by gelatin, polypropylene, and polyethylene terephthalate. Gelatin, polypropylene, polyethylene, and polyethylene terephthalate do not have air permeability, and are suitable for the formation of a thin film. Further, gelatin, polypropylene, polyethylene, and polyethylene terephthalate are able to acquire sufficient durability against the moisture contained in the tobacco source 131. Polypropylene, polyethylene, and polyethylene terephthalate particularly have excellent water resistance. In addition, gelatin, polypropylene, and polyethylene have resistance to bases, and hence not tend to be degraded by the basic component even if the tobacco source 131 has a basic component.

The predetermined film 133 preferably has a film thickness of 0.1 μm or more and 0.3 μm or less. As a result, it is possible to easily destruct a part of the predetermined film 133 while maintaining the function of protecting the tobacco source 131 by the predetermined film 133.

As described above, the predetermined film 133 is integrally formed with the filter 132, however, the predetermined film 133, for example, is affixed on to the filter 132 by glue, or the like. Alternatively, the outer shape of the predetermined film 133 may be set to be smaller than the outer shape of the filter 132 in the vertical direction to the predetermined direction A so as to pack the filter 132 within the predetermined film 133, and fit the filter 132 within the predetermined film 133 by the restoring force of the filter 132. Else, an engagement portion for engaging the predetermined film 133 may be provided in the filter 132.

Here, although the shape of the predetermined film 133 is not particularly restricted, the predetermined film 133 preferably has a concave shape in the vertical cross-section with respect to the predetermined direction A. In such a case, after packing the tobacco source 131 inside the predetermined film 133 having a concave shape, the opening of the predetermined film 133 in which the tobacco source 131 is packed is closed by the filter 132.

When the predetermined film 133 has a concave shape in the vertical cross-section with respect to the predetermined direction A, of the cross-sectional area of the space enclosed by the predetermined film 133, the maximum cross-sectional area (that is, the cross-sectional area of the opening in which the filter 132 is fitted) is preferably 25 mm$^2$ or more and 80 mm$^2$ or less, and more preferably 25 mm$^2$ or more and 55 mm$^2$ or less. In such a case, the cross-sectional area of the filter 132 in the vertical cross-section with respect to the predetermined direction A is preferably 25 mm$^2$ or more and 55 mm$^2$ or less. The thickness of the filter 132 in the predetermined direction A is preferably 3.0 mm or more and 7.0 mm or less.

The mouthpiece unit 140 has a mouthpiece hole 141. The mouthpiece hole 141 is an opening configured to expose the filter 132. By inhaling aerosol from the mouthpiece hole 141, the user inhales the flavor together with the aerosol.

In the first embodiment, the mouthpiece unit 140 is configured in a removable manner with respect to the outer wall 124 of the atomization unit 120. For example, the mouthpiece unit 140 has a cup shape that is configured to fit in the inner surface of the outer wall 124. However, the embodiment is not limited thereto. The mouthpiece unit 140 may be attached to the outer wall 124 in a rotatable manner with the help of a hinge, etc.

In the first embodiment, the mouthpiece unit 140 is provided as a separate part from the capsule unit 130. That is, the mouthpiece unit 140 configures a part of the main body unit. However, the embodiment is not limited thereto. The mouthpiece unit 140 may be integrally provided with the capsule unit 130. In such a case, it must be noted that the mouthpiece unit 140 configures a part of the capsule unit 130.

As described above, in the first embodiment, the non-burning type flavor inhaler 100 has the outer wall 124 (housing) of the atomization unit 120 having the air flow path 122 that continues from the air lead-in hole 125 (inlet) to the mouthpiece hole 141 (outlet). In the first embodiment, the air flow path 122 is configured by the atomization unit 120, but the aspect of the air flow path 122 is not limited thereto. The air flow path 122 may be configured by both a housing of the electrical unit 110, and a housing of the atomization unit 120.

(Control Circuit)

Figure 4:
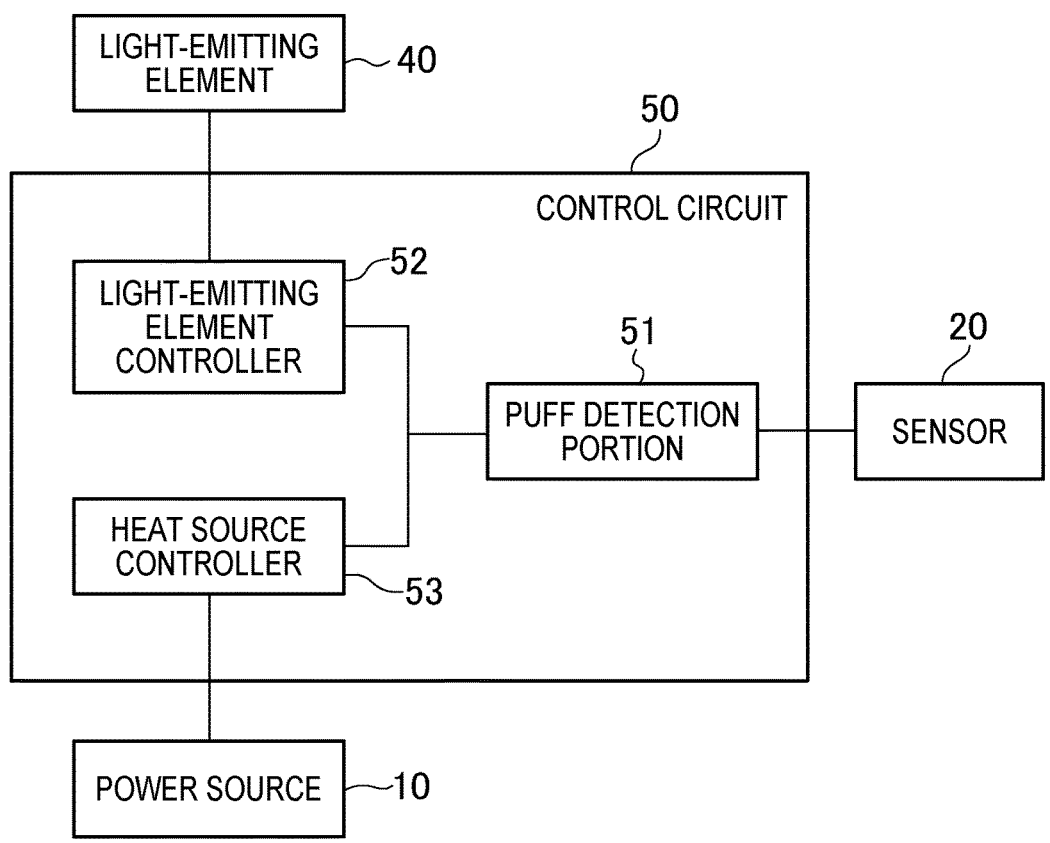
FIG. 4 is a block diagram showing a control circuit 50 according to the first embodiment.

A control circuit according to the first embodiment will be described, below. FIG. 4 is a block diagram showing a control circuit 50 according to the first embodiment.

As shown in FIG. 4, the control circuit 50 has a puff detection portion 51, a light-emitting element controller 52, and a heat source controller 53.

The puff detection portion 51 is connected to the sensor 20 configured to output the electric capacitance of the capacitor changed depending on the puff action of the user. The puff detection portion 51 detects, on the basis of an output value that is output from the sensor 20, a puffing state. Specifically, the puff detection portion 51 detects a puffing state in which an aerosol is inhaled (puff duration) and a non-puffing state in which an aerosol is not inhaled (non-puff duration). As a result, the puff detection portion 51 is capable of specifying the number of times of the puff actions of inhaling an aerosol. Further, the puff detection portion 51 is also capable of detecting a required time of a one-time puff action of inhaling an aerosol.

In the first embodiment, the puff detection portion 51 detects, on the basis of the output value that is output from the sensor 20, the start or the end of the puff duration. Here, the output value is a voltage value indicating the electric capacitance of the capacitor.

Specifically, the puff detection portion 51 detects the start or the end of the puff duration, when an inclination configured by two or more output values that are output from the sensor 20 has a predetermined sign (here, negative), and an absolute value of the inclination having the predetermined sign (here, negative) is larger than a predetermined value. In other words, the puff detection portion 51 detects the start of the puff duration when the above-described condition is satisfied before the detection of the start of the puff duration. On the other hand, the puff detection portion 51 detects the end of the puff duration when the above-described condition is satisfied after the detection of the start of the puff duration.

Here, a condition (predetermined value) used for the start of the puff duration may either be the same or different from a condition (predetermined value) used for the end of the puff duration. Further, the determination of the end of the puff duration is preferably performed after the lapse of a predetermined time period (for example, 200 msec to 500 msec) from the detection of the start of the puff duration. As a result, a situation is prevented where the end of the puff duration is erroneously detected immediately after the detection of the start of the puff duration.

Figure 5:
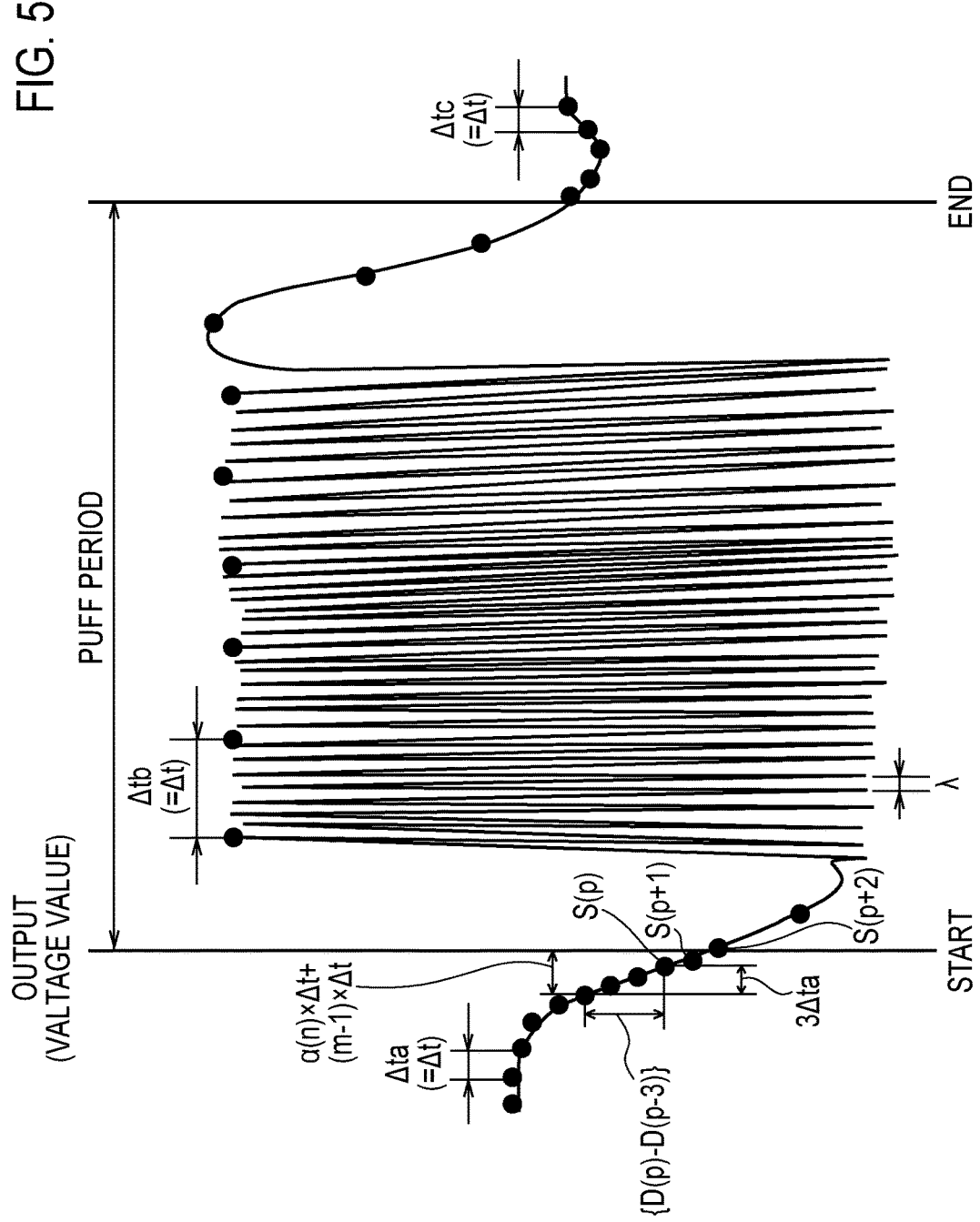
FIG. 5 is a diagram for describing a detection of a puff duration according to the first embodiment.

In particular, as shown in FIG. 5, the puff detection portion 51 monitors the output value that is output from the sensor 20 in a sampling cycle ($\Delta t$). In FIG. 5, it must be noted that a voltage value is illustrated as an output value that is output from the sensor 20. A sampling cycle ($\Delta ta$) in which the output value that is output from the sensor 20 is monitored before the detection of the start of the puff duration is shorter than a sampling cycle ($\Delta tb$) in which the output value that is output from the sensor 20 is monitored after the detection of the start of the puff duration. A sampling cycle ($\Delta tc$) in which the output value that is output from the sensor 20 is monitored after the detection of the end of the puff duration is shorter than the sampling cycle ($\Delta tb$) in which the output value that is output from the sensor 20 is monitored before the detection of the end of the puff duration.

It is noted that the sampling cycle ($\Delta ta$) in which the output value that is output from the sensor 20 is monitored before the detection of the start of the puff duration is similar to the sampling cycle ($\Delta tc$) in which the output value that is output from the sensor 20 is monitored after the detection of the end of the puff duration. Further, the sampling cycle ($\Delta tb$) in which the output value that is output from the sensor 20 is monitored after the detection of the start of the puff duration is similar to the sampling cycle ($\Delta tb$) in which the output value that is output from the sensor 20 is monitored before the detection of the end of the puff duration. In other words, the sampling cycle ($\Delta ta$ or $\Delta tc$) in which the output value that is output from the sensor 20 is monitored outside the puff duration is shorter than the sampling cycle ($\Delta tb$) in which the output value that is output from the sensor 20 is monitored within the puff duration. The sampling cycle ($\Delta ta$ or $\Delta tc$) in which the output value that is output from the sensor 20 is monitored outside the puff duration is, for example, 1 msec, and the sampling cycle ($\Delta tb$) in which the output value that is output from the sensor 20 is monitored within the puff duration is, for example, 10 msec.

Hereinafter, each symbol represents the below-mentioned contents. $\Delta t$ represents a cycle in which the output value that is output from the sensor 20 is monitored, $D(n)$ represents the output value that is output from the sensor 20 in time $t(n)$, $\alpha(n)$ represents a positive integer, and $S(n)$ represents an inclination configured by the output value that is output from the sensor 20 in time $t(n)$. It is noted that n represents the calculation frequency of $S(n)$. Further, $\alpha(n)$ may be a constant value (for example, 3), or may change every time $S(n)$ is calculated.

Under such a prerequisite, the puff detection portion 51 may calculate, by $S(n)=\{D(n)-D(n-\alpha(n)\times\Delta t)\}/(\alpha(n)\times\Delta t)$, the inclination configured by the output value that is output from the sensor 20. It must be noted that $D(n-\alpha(n)\times\Delta t)$ represents the output value that is monitored only "$\alpha(n)\times\Delta t$" time before the time $t(n)$.

In such a case, the puff detection portion 51 detects the start of the puff duration, when, for consecutive m times (m is an integer value of 2 or more) of $S(n)$, a condition is satisfied before the detection of the start of the puff duration, in which all $S(n)$s are the value of a predetermined sign (here, negative), and the absolute value of all $S(n)$s is larger than a first value that is described later. Here, it must be noted that the sampling cycle ($\Delta t$) used when detecting the start of the puff duration is $\Delta ta$ (or $\Delta tc$). On the other hand, the puff detection portion 51 detects the end of the puff duration, when, for consecutive m times of $S(n)$, a condition is satisfied after the detection of the start of the puff duration, in which all S(n)s are the value of a predetermined sign (here, negative), and the absolute value of all S(n)s is larger than the first value. Here, it must be noted that the sampling cycle ($\Delta t$) used when detecting the end of the puff duration is $\Delta tb$ (>$\Delta ta$ or $\Delta tc$).

For example, a case of detection of the start of the puff duration when $\alpha(n)$=3 and m=3 will be described while referencing FIG. 5. In such a case, since all of S(p), S(p+1), and S(p+2) have a negative value, and the absolute values of all of S(p), S(p+1), and S(p+2) are larger than the first value, the start of the puff duration is detected in time p+2. It is noted that as a calculation method of S(n), if an explanation is provided using time p as an example, then S(p) is calculated by $S(p)=\{D(p)-D(p-3)/3\Delta t\}$.

It is noted that the first value is a predetermined value that is decided beforehand, and may be set appropriately depending on the type, etc. of the sensor 20. Further, a cycle by which the puff detection portion 51 calculates S(n) may be same as the sampling cycle ($\Delta t$), or may be different from the sampling cycle ($\Delta t$). It is noted that the cycle by which the puff detection portion 51 calculates S(n) is preferably an integral multiple of the sampling cycle ($\Delta t$).

It is noted that the sampling cycle ($\Delta t$) and a calculation cycle of S(n) are possible to be set appropriately. While it is preferable that the sampling cycle ($\Delta t$) and the calculation cycle of S(n) are synchronous, the sampling cycle ($\Delta t$) and the calculation cycle of S(n) may not necessarily be synchronous. Further, a cycle in which the sensor 20 outputs the output value is also possible to be set appropriately. In addition, the sensor 20 may repeatedly turn ON/OFF in synchronization with the sampling cycle ($\Delta t$) and the calculation cycle of S(n), or may be ON at all times.

In the first embodiment, a sampling cycle (for example, 5 msec.) of the output value that is referenced during the determination of the start or end of the puff duration is preferably longer than a predetermined time. Specifically, the sampling cycle of the output value that is referenced when determining the start or end of the puff duration is represented by $\alpha(n)\times\Delta t+(m-1)\times\Delta t$, as shown in FIG. 5. The predetermined time period is preferably longer than ½ of the average value of a wavelength ($\lambda$ shown in FIG. 5) of a frequency of a waveform derived from a continuous approximation function, where the continuous approximation function is derived, under the prerequisite that the output value that varies in the puff duration is discretely acquired on the time axis, from the plot of the output value acquired discretely. Thus, by setting a lower limit for the sampling cycle of the output value that is referenced when determining the start or the end of the puff duration, the fact is prevented that the above-described conditions are accidently satisfied before the detection of the start of puff duration by an event that is different from the puff action of the user (for example, the vibration of human voice, etc.), and the accuracy of detection of the start of the puff duration is improved. Further, even after the detection of the start of the puff duration, the fact is prevented that the above-described conditions are accidently satisfied before the user actually ends the puff action, and the accuracy of detection of the end of the puff duration is improved.

In the first embodiment, the puff detection portion 51 preferably detects the start or the end of the puff duration, when, for one time of the consecutive m times of S(n), a condition is satisfied in which an absolute value of S(n) is smaller than a second value. The second value is preferably a value that is sufficiently larger than the first value, and that is an average value of an inclination (absolute value) configured by two or more output values that vary in a puff duration. In other words, the puff detection portion 51 does not detect the start or the end of the puff duration, when, for all of the consecutive m times of S(n)s, S(n) is a value of a predetermined sign (here, negative), and an absolute value of S(n) is equal to or larger than the second value. On the other hand, the puff detection portion 51 detects the start or the end of the puff duration, when, for consecutive m times of S(n), a condition is satisfied in which all S(n)s are larger than the first value, and a condition is also satisfied in which the absolute value of at least one time of S(n) is smaller than the second value. As a result, even when the electric capacitance of the sensor 20 changes rapidly due to an event that is different from the puff action, the erroneous detection of the start or the end of the puff duration is controlled. An event that is different from the puff action implies, for example, an event where in a case in which the non-burning type flavor inhaler 100 is kept on a table, the electric capacitance of the sensor 20 changes due to the vibrations on the table, and an event where rather than inhaling, the user performs blowing from the mouthpiece of the non-burning type flavor inhaler 100.

In the first embodiment, the sampling cycle of the output value that is referenced when determining the start or end of the puff duration is $\alpha(n)\times\Delta t+(m-1)\times\Delta t$. That is, the sampling cycles of the output values that are referenced during the calculation of consecutive two times of S(n) of m times of S(n) partially overlap each other, and $\alpha(n)$ is 2 or more. As a result, as compared to a case in which the sampling cycles of the output values that are referenced during the calculation of consecutive two times of S(n) do not overlap, that is, a case in which the sampling cycle of the output value that is referenced when determining the start or the end of the puff duration is $\alpha(n)\times\Delta t\times m$, the sampling cycle ($\alpha(n)\times\Delta t+(m-1)\times\Delta t$) of the output value that is referenced when determining the start or the end of the puff duration is shorter, because of which it is possible to quickly detect the start of the puff duration, and thus, the detection accuracy of the start of the puff duration is improved. In addition, as compared to a case in which $\alpha(n)$ is 1, a slight variation in the output value is not detected as the start of the puff duration, and therefore, it is possible to prevent the erroneous detection of the puff duration.

The light-emitting element controller 52 is connected to the light-emitting element 40 and the puff detection portion 51, and controls the light-emitting element 40. Specifically, the light-emitting element controller 52 controls the light-emitting element 40 according to a first light-emitting mode, in the puffing state in which aerosol is inhaled. On the other hand, the light-emitting element controller 52 controls the light-emitting element 40 according to a second light-emitting mode that is different from the first light-emitting mode, in the non-puffing state in which aerosol is not inhaled.

Here, the light-emitting mode is defined according to a combination of parameters such as the amount of light of the light-emitting element 40, the number of the light-emitting elements 40 that are in the lit-up state, the color of the light-emitting element 40, the cycle of repetition of lighting up of the light-emitting element 40 and lighting out of the light-emitting element 40, etc. A different light-emitting mode implies a light-emitting mode in which any one of the above-described parameters is different.

In the first embodiment, the second light-emitting mode changes in accordance with the number of times of the puff action of inhaling aerosol. The first light-emitting mode may change in accordance with the number of times of the puff action of inhaling aerosol, or may be fixed regardless of the number of times of the puff action of inhaling aerosol.

For example, the first light-emitting mode is a mode in which a red-colored light-emitting element 40 is lit up in order to imitate the sense of use of a regular cigarette in which aerosol is generated in association with burning. The first light-emitting mode is preferably a mode in which the light-emitting element 40 is continuously lit up. Alternatively, the first light-emitting mode may be a mode in which lighting up of the light-emitting element 40 and lighting out of the light-emitting element 40 are repeated in a first cycle.

For example, the second light-emitting mode is a mode in which a blue-colored light-emitting element 40 is lit up in order to notify the user that the aerosol source is not heated up. The second light-emitting mode may be a mode in which lighting up of the light-emitting element 40 and lighting out of the light-emitting element 40 are repeated in a second cycle that is longer than the first cycle.

As described above, the second light-emitting mode changes in accordance with the number of times of the puff action of inhaling aerosol.

For example, the second light-emitting mode may be a mode in which the number of light-emitting elements 40 that are to be controlled increases with an increase in the number of times of the puff action. For example, the light-emitting element controller 52 controls one light-emitting element 40 by the second light-emitting mode in the first puff action, and controls two light-emitting elements 40 by the second light-emitting mode in the second puff action. Alternatively, the light-emitting element controller 52 controls n number of light-emitting elements 40 by the second light-emitting mode in the first puff action, and controls n−1 number of light-emitting elements 40 by the second light-emitting mode in the second puff action.

Alternatively, the second light-emitting mode may be a mode in which the amount of light of the light-emitting element 40 either increases or decreases with an increase in the number of times of the puff action. Else, the second light-emitting mode may be a mode in which the color of the light-emitting element 40 changes with an increase in the number of times of the puff action.

It is noted that even when the first light-emitting mode changes in accordance with the number of times of the puff action, the change in the first light-emitting mode is basically the same concept as the change in the second light-emitting mode.

In the first embodiment, when the number of times of the puff action of inhaling the aerosol reaches a predetermined number of times (for example, eight times), the light-emitting element controller 52 ends the control complying with the first light-emitting mode and the second light-emitting mode, and controls the light-emitting element 40 with an end light-emitting mode.

The end light-emitting mode is preferably different from the first light-emitting mode and the second light-emitting mode as long as the end light-emitting mode is a mode for notifying the user that it is time to end the puff action. For example, the end light-emitting mode is a mode in which the amount of light of the light-emitting element 40 is smaller than the first light-emitting mode and the second light-emitting mode, and the amount of light of the light-emitting element 40 reduces over time.

The heat source controller 53 is connected to the power source 10, and controls the power source output (here, the amount of electric power) from the power source 10 to the heat source 80 (atomizer). It is noted that the amount of electric power is the result of multiplication of time and electric power (voltage or current), and is a value that is controlled by time and electric power. For example, the heat source controller 53 controls the voltage applied to the heat source 80 from the power source 10 by controlling the DC-DC converter, etc. that is arranged together with the power source 10.

Here, in a case where a voltage is applied continuously to the heat source 80 (atomizer), the amount of power source output (integrated value) is defined by the value of the voltage applied to the heat source 80 (atomizer) and the time for which the supply of the power source output continues. On the other hand, in a case (pulse control) where a voltage is applied intermittently to the heat source 80 (atomizer), the amount of power source output (integrated value) is defined by the value of the voltage applied to the heat source 80 (atomizer), the pulse width, the pulse interval, and the time for which the supply of the power source output continues.

It must be noted that in the first embodiment, the heat source controller 53 starts the supply of the power source output from the power source 10 to the heat source 80 in the puff duration during which a puff action is performed, and the heat source controller 53 stops the supply of the power source output from the power source 10 to the heat source 80 in the non-puff duration during which a puff action is not performed.

Firstly, the heat source controller 53 gradually increases the power source output to the heat source 80 from the standard power source output in association with an increase in the number of times of the puff action of inhaling the aerosol. As a result, it becomes possible to imitate the sense of use of a regular cigarette configured to generate aerosol in association with burning.

Here, the heat source controller 53 may control the power source 10 in such a way that when a puff action is performed after the number of times of the puff action exceeds the predetermined number of times, a power source output that is smaller than the standard power source output is supplied to the heat source 80. As a result, even if it is time to end the puff action, the user is capable of inhaling just a small amount of the aerosol, by which it is possible to increase the level of satisfaction of the user.

When a predetermined time period has elapsed after the number of times of the puff action exceeds a predetermined number of times, the heat source controller 53 turns OFF the power source of the non-burning type flavor inhaler 100. As a result, the waste of electric power of the non-burning type flavor inhaler 100 due to forgetting to turn off the power source of the non-burning type flavor inhaler 100 is controlled.

Here, the heat source controller 53 may combine the above-described actions to supply a power source output that is smaller than the standard power source output to the heat source 80 after the number of times of the puff action exceeds a predetermined number of times, and to turn OFF the power source of the non-burning type flavor inhaler 100 after the number of times of the puff action exceeds the predetermined number of times as well as when the predetermined time has elapsed.

The heat source controller 53 preferably increases the gradient of the power source output to the heat source 80 with an increase in the number of times of the puff action of inhaling the aerosol. Here, the gradient of the power source output is defined by the number of times of the puff action during which a fixed power source output is maintained, and the increment by which the power source output increases. That is, there is a reduction, with an increase in the number of times of the puff action, in the number of times of the puff action during which a fixed power source output is maintained. Alternatively, there is an increase, with an increase in the number of times of the puff action, in the increment by which the power source output increases. Alternatively, with an increase in the number of times of the puff action, there is a reduction in the number of times of the puff action during which a fixed power source output is maintained, and an increase in the increment by which the power source output increases.

In addition, the heat source controller 53 may control a first mode in which a first standard power source output is used as the standard power source output, and a second mode in which a second standard power source output that is greater than the first standard power source output is used as the standard power source output. Three or more stages of the standard power source output may be prepared as the standard power source output. In such a case, the switching of the standard power source output may be performed by an operation of the push button 30. For example, the first mode may be applied by pushing the push button 30 one time, and the second mode may be applied by pushing the push button 30 twice. Further, the push button 30 may be substituted by a touch sensor. The power source of the non-burning type flavor inhaler 100 may also be turned ON by performing the above-described operations. That is, turning ON of the power source and switching of the standard power source output may be performed by a single action by operating the push button 30. However, the action of turning ON the power source by operating the push button 30 may be separate from the action of switching the standard power source output.

Secondly, the heat source controller 53 controls a standard mode that must be applied to a user for whom the required time of a one-time puff action for inhaling aerosol is within the standard required time duration, and a shortened mode that must be applied to a user for whom the required time of a one-time puff action for inhaling aerosol is shorter than the standard required time duration. Here, the standard required time duration implies a time duration when the balance of the amount of supply of the aerosol (amount of TPM (Total Particulate Matter)) is particularly good.

Specifically, in a one-time puff action of the standard mode, the heat source controller 53 controls the power source 10 such that the standard power source output is supplied to the heat source 80 for the duration until a first time period elapses, and controls the power source 10 such that a power source output that is smaller than the standard power source output is supplied to the heat source 80 for the duration after the first time period has elapsed. It is noted that for the duration after the first time period has elapsed, the heat source controller 53 may immediately set the power source output to the heat source 80 to zero, or may reduce the power source output to the heat source 80 over time.

Here, the first time period is preferably same as the end timing of the above-described standard required time duration. However, the first time period may be longer than the end timing of the standard required time duration within a range in which the balance of the amount of supply of the aerosol (the TPM amount) is permitted.

On the other hand, in a one-time puff action of the shortened mode, the heat source controller 53 controls the power source 10 such that a first power source output that is greater than the standard power source output is supplied to the heat source 80 for the duration until a second time period elapses, and controls the power source 10 such that a second power source output that is smaller than the first power source output is supplied to the heat source 80 for the duration until a third time period after the second time period elapses, and also controls the power source 10 such that a power source output that is smaller than the second power source output is supplied to the heat source 80 for the duration after the third time period has elapsed. It is noted that for the duration after the third time period has elapsed, the heat source controller 53 may immediately set the power source output to the heat source 80 to zero, or may reduce the power source output to the heat source 80 over time.

Here, the second time period is preferably shorter than the start timing of the above-described standard required time duration. However, the second time period may be included in the standard required time duration, or may be longer than the end timing of the standard required time duration. The third time period is preferably same as the end timing of the above-described standard required time duration. However, the third time period may be longer than the end timing of the standard required time duration within a range in which the balance of the amount of supply of the aerosol (the TPM amount) is permitted. Further, the second power source output that is smaller than the first power source output may be the same as the above-described standard power source output. However, the second power source output may be greater than the standard power source output, or may be smaller than the standard power source output.

It is noted that as described above, the heat source controller 53 gradually increases the power source output to the heat source 80 from the standard power source output with an increase in the number of times of the puff action. In other words, it must be noted that the standard power source output in a one-time puff action increases an increase in the number of times of the puff action.

The heat source controller 53 may set the standard mode or the shortened mode depending on the learning of the puff action by the user. In particular, when the required time of a one-time puff action that is acquired by learning is within the standard required time duration, the heat source controller 53 sets the standard mode. When the required time of a one-time puff action that is acquired by learning is shorter than the standard required time duration, the heat source controller 53 sets the shortened mode.

In the first embodiment, the atomization unit 120 is removable with respect to the electrical unit 110. Further, the capsule unit 130 is removable with respect to the main body unit including the electrical unit 110. In other words, it is possible to reuse the electrical unit 110 over a plurality of times of puff action series. A puff action series is a series of actions in which the puff action is repeated a predetermined number of times. Therefore, by learning the required time of a one-time puff action in the first puff action series, the standard mode or the shortened mode may be set in the second puff action series or thereafter. Alternatively, by learning the required time of a one-time puff action in the first n-time puff actions in a one-time puff action series, the standard mode or the shortened mode may be set for the n+1 (or, n+2)th puff action or thereafter.

Alternatively, the heat source controller 53 may set the standard mode or the shortened mode depending on the operation by the user. In such a case, a switch for switching the standard mode and the shortened mode is provided in the non-burning type flavor inhaler 100. It is noted that the switching of the standard mode and the shortened mode may be permitted in a one-time puff action series. Alternatively, the mode that is set initially may be applied in a fixed manner without permitting the switching of the standard mode and the shortened mode in a one-time puff action series.

(Light-emitting Mode)

An example of a light-emitting mode according to the first embodiment will be described, below. FIG. 6 and FIG. 7 are diagrams showing an example of the light emitting mode according to the first embodiment. FIG. 6 and FIG. 7 illustrate a case in which a user must end a puff action series, in principle, when the number of times of the puff action reaches eight times (a predetermined number of times).

Firstly, a first example of the light-emitting mode will be described with reference to FIG. 6. As shown in FIG. 6, a first light-emitting pattern in the puffing state is fixed regardless of the number of times of the puff action. On the other hand, a second light-emitting pattern in the non-puffing state changes in accordance with the number of times of the puff action.

For example, as shown in FIG. 6, in a non-puffing state #1 to a non-puffing state #4, a light-emitting mode #2-1 is used as the second light-emitting mode. In a non-puffing state #5 to a non-puffing state #7, a light-emitting mode #2-2 is used as the second light-emitting mode. In a non-puffing state #8, a light-emitting mode #2-3 is used as the second light-emitting mode. It is noted that in the ninth non-puffing state and thereafter, the above-described end light-emitting mode is used.

On the other hand, in a puffing state #1 to a puffing state #8, a light-emitting mode #1 is used as the first light-emitting mode. Even in the ninth puffing state and thereafter, the light-emitting mode #1 may be used as the first light-emitting mode, or a light-emitting mode different from the first light-emitting mode and the second light-emitting mode maybe used in order to indicate that the puff is in excess of eight times (predetermined number of times).

The light-emitting mode #1, the light-emitting mode #2-1, the light-emitting mode #2-2, the light-emitting mode #2-3, and the end light-emitting mode are different light-emitting modes to each other. As described above, the light-emitting mode is defined according to a combination of parameters such as the amount of light of the light-emitting element 40, the number of the light-emitting elements 40 that are in the lit-up state, the color of the light-emitting element 40, the cycle of repetition of lighting up of the light-emitting element 40 and lighting out of the light-emitting element 40, etc. A different light-emitting mode implies a light-emitting mode in which any one of the above-described parameters is different.

For example, the light-emitting mode #1 is preferably a light-emitting mode that offers an image of burning in order to imitate the sense of use of a regular cigarette in which aerosol is generated in association with burning. The light-emitting mode #2-1 is a light-emitting mode that offers an image of an initial stage of the puff action series, the light-emitting mode #2-2 is a light-emitting mode that offers an image of a middle stage of the puff action series, and the light-emitting mode #2-3 is a light-emitting mode that offers an image of an end stage of the puff action series. The end light-emitting mode is preferably a mode for notifying the user that it is time to end the puff action.

Secondly, the first example of the light-emitting mode will be described with reference to FIG. 7. As shown in FIG. 7, both the first light-emitting pattern in the puffing state and the second light-emitting pattern in the non-puffing state change in accordance with the number of times of the puff action.

For example, as shown in FIG. 7, in the non-puffing state, the light-emitting mode #2-1, the light-emitting mode #2-2, and the light-emitting mode #2-3 are used as the second light-emitting mode, in a similar manner of the case shown in FIG. 6.

On the other hand, in the puffing state #1 to the puffing state #4, a light-emitting mode #1-1 is used as the first light-emitting mode. In a puffing state #5 to a puffing state #7, a light-emitting mode #1-2 is used as the first light-emitting mode. In a puffing state #8, a light-emitting mode #1-3 is used as the first light-emitting mode. It is noted that in the ninth puffing state and thereafter, a light-emitting mode #1-4 is used.

It is preferable that the light-emitting mode #1-1 is a light-emitting mode that offers an image of an initial stage of the puff action series, the light-emitting mode #1-2 is a light-emitting mode that offers an image of a middle stage of the puff action series, and the light-emitting mode #1-3 is a light-emitting mode that offers an image of an end stage of the puff action series. It is noted that, similarly to the end light-emitting mode, the light-emitting mode #1-4 is preferably a mode for notifying the user that it is time to end the puff action.

As shown in FIG. 6 and FIG. 7, the first embodiment illustrates a case in which the light-emitting mode in the non-puffing state #1 (that is, the non-puffing state immediately after turning ON the power source of the non-burning type flavor inhaler 100) is the second light-emitting mode (light-emitting mode #2-1). However, the embodiment is not limited thereto. The light-emitting mode in the non-puffing state #1 may be a start light-emitting mode that is different from the second light-emitting mode. The start light-emitting mode is preferably a mode for notifying the user that preparations have been made to start the puff action.

(Power Control in Puff Action Series)

Figure 8:
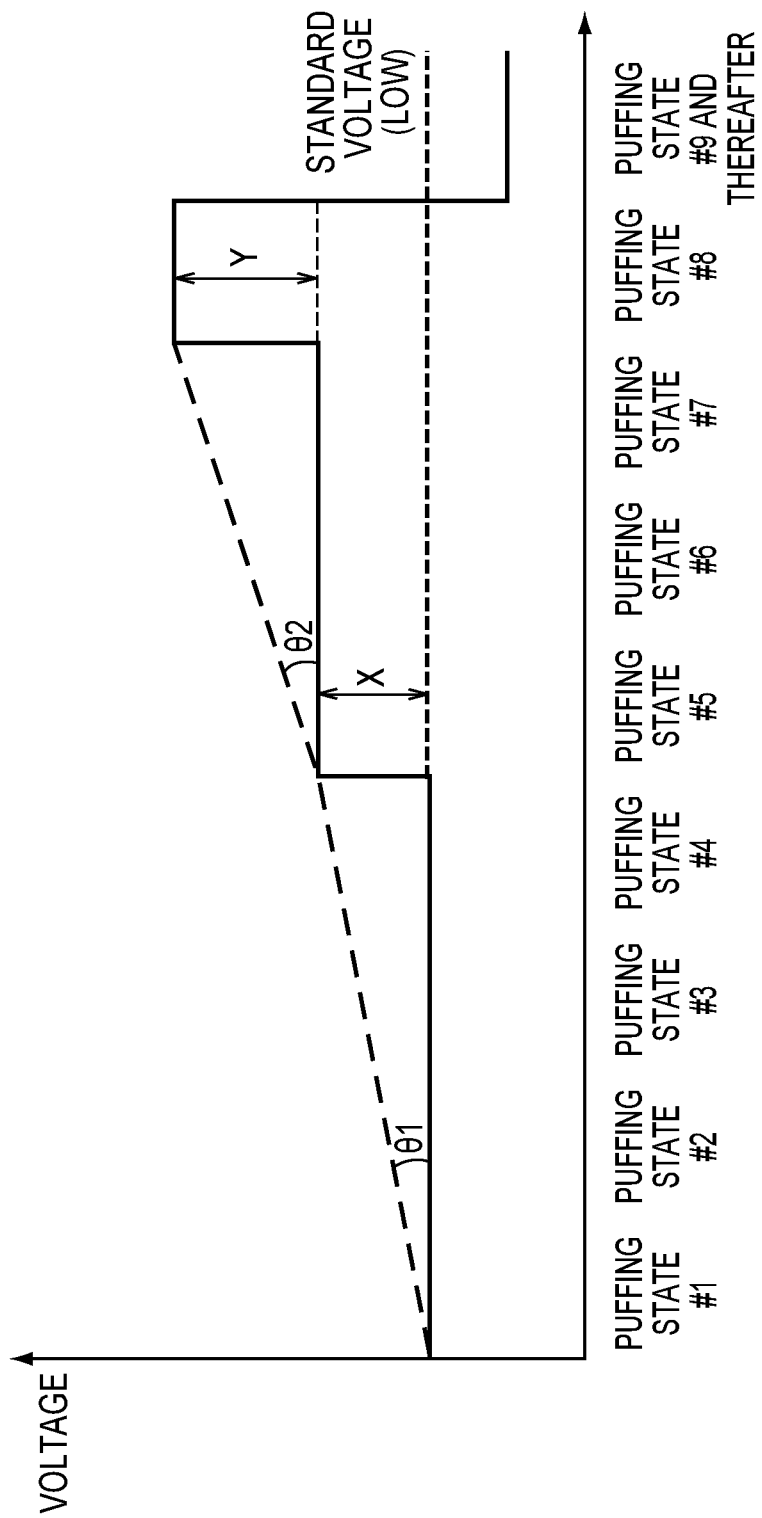
FIG. 8 is a diagram showing an example of power control in a puff action series according to the first embodiment.
Figure 9:
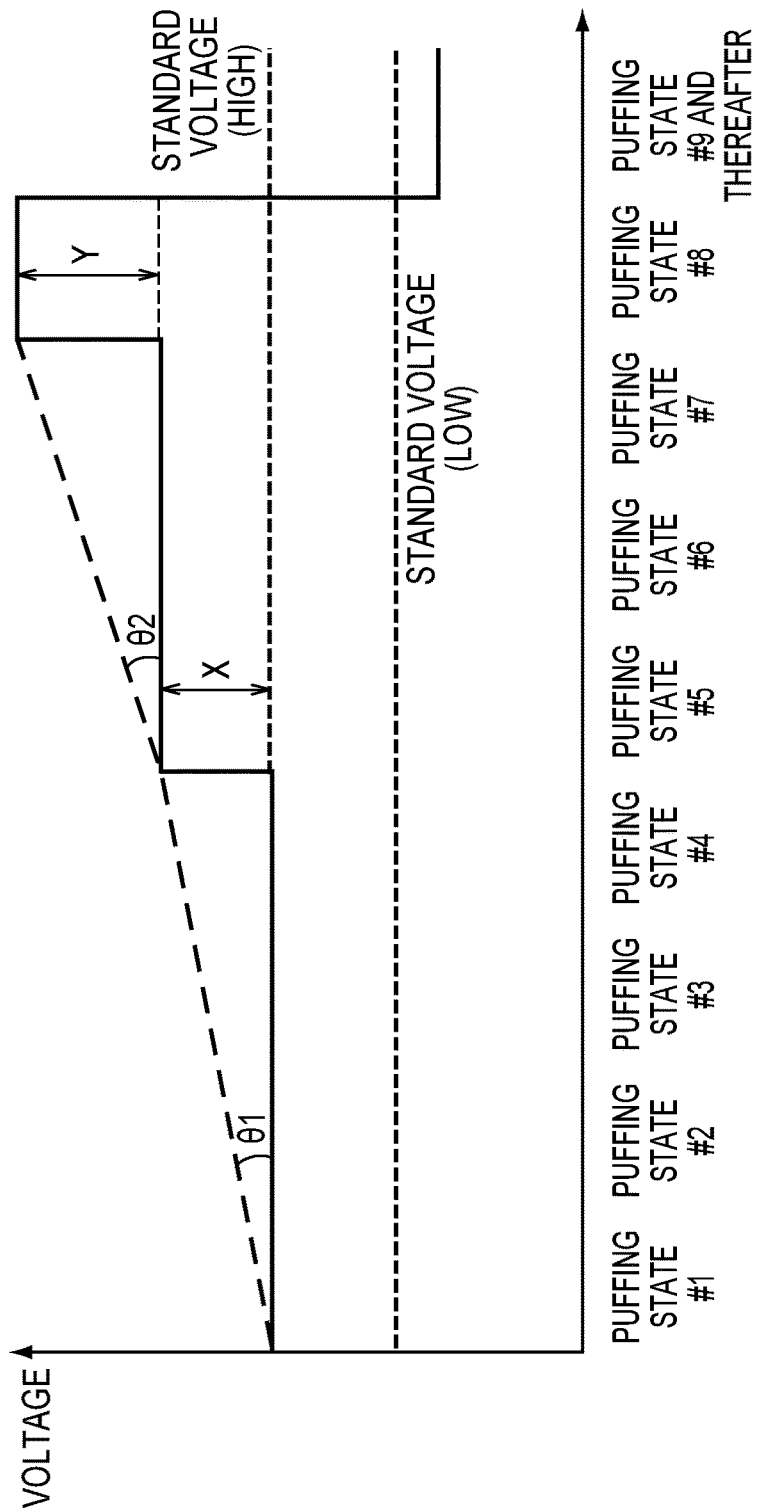
FIG. 9 is a diagram showing an example of power control in the puff action series according to the first embodiment.

An example of power control in a puff action series according to the first embodiment will be described, below. FIG. 8 and FIG. 9 are diagrams showing an example of power control in the puff action series according to the first embodiment. FIG. 8 and FIG. 9 illustrate a case in which the user must end a puff action series, in principle, when the number of times of the puff action reaches eight times (a predetermined number of times). Further, it must be noted that the behavior of the power source output in the non-puffing state is omitted in FIG. 8 and FIG. 9 since the power source output is not supplied to the heat source 80 in the non-puffing state.

Here, a case in which the power source output supplied to the heat source 80 is controlled depending on the voltage applied to the heat source 80 will be illustrated. Therefore, in the first embodiment, it may be assumed that the power source output is synonymous with voltage. Further, FIG. 8 shows the first mode (Low mode) in which a first voltage is used as the standard voltage, and FIG. 9 shows a second mode (High mode) in which a second voltage that is higher than the first voltage is used as the standard voltage. It is noted that the standard voltage is different, but the behavior of the voltage applied to the heat source 80 is similar in the first mode (Low mode) and the second mode (High mode).

As shown in FIG. 8 and FIG. 9, the heat source controller 53 gradually increases the voltage applied to the heat source 80 from the standard voltage with an increase in the number of times of the puff action of inhaling the aerosol. Specifically, in the puffing state #1 to the puffing state #4, the voltage applied to the heat source 80 is fixed, and the standard voltage is applied to the heat source 80. In the puffing state #5 to the puffing state #7, the voltage applied to the heat source 80 is fixed, and a voltage that is one step larger than the standard voltage is applied to the heat source

80. In the puffing state #8, a voltage that is two steps larger than the standard voltage is applied to the heat source 80. In the ninth puffing state and thereafter, a voltage that is smaller than the standard voltage is applied to the heat source 80.

As described above, the heat source controller 53 increases the gradient of the voltage applied to the heat source 80 with an increase in the number of times of the puff action of inhaling the aerosol.

For example, there is a reduction, with an increase in the number of times of the puff action, in the number of times of the puff action during which a fixed voltage is maintained. That is, the number of times of the puff action during which the standard voltage is applied is four, the number of times of the puff action during which a voltage that is one step larger than the standard voltage is applied is three, and the number of times of the puff action during which a voltage that is two steps larger than the standard voltage is applied is one. Alternatively, there is a reduction, with an increase in the number of times of the puff action, in the number of times of the puff action during which a fixed voltage is maintained. Alternatively, an increment Y of the voltage at the second time is larger than an increment X of the voltage of the first step.

As a result, there is an increase, with an increase in the number of times of the puff action, in the gradients (θ1 and θ2) of the voltage defined by the number of times of the puff action during which a fixed voltage is maintained, and the increment by which the voltage increases. In other words, the gradient θ2 of the middle stage of the puff action series is larger than the gradient θ1 of the initial stage of the puff action series.

In FIG. 8 and FIG. 9, the number of steps in which the voltage applied to the heat source 80 increases is two; however, the embodiment is not limited thereto. The number of steps in which the voltage applied to the heat source 80 increases may be three or more. Alternatively, the number of steps in which the voltage applied to the heat source 80 increases may be one.

(Power Control in one-time Puff Action)

Figure 10:
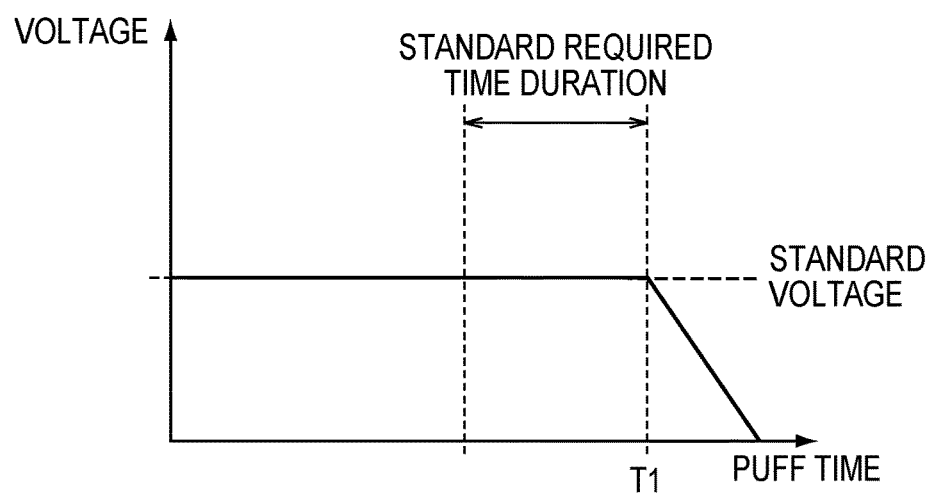
FIG. 10 is a diagram showing an example of power control in a one-time puff action according to the first embodiment.
Figure 11:
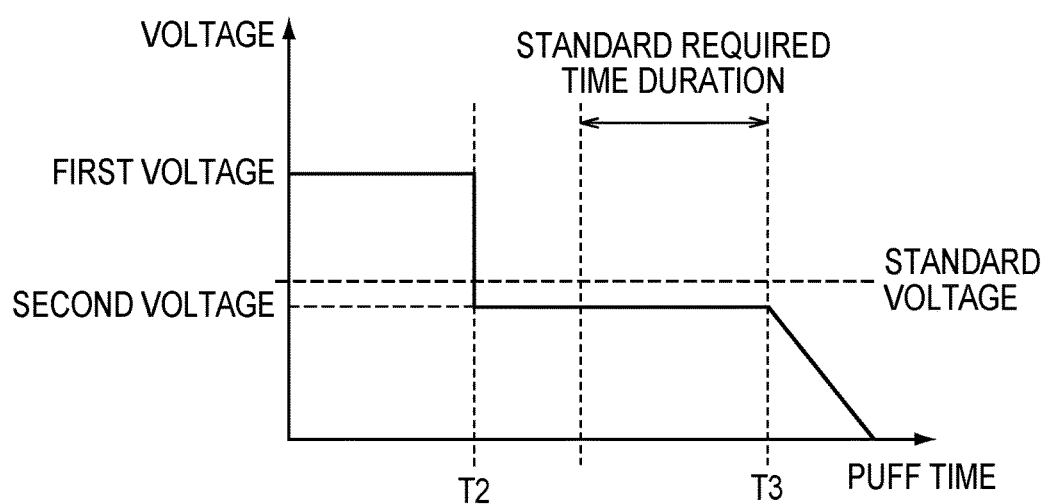
FIG. 11 is a diagram showing an example of power control in the one-time puff action according to the first embodiment.

An example of power control in a one-time puff action according to the first embodiment will be described, below. FIG. 10 and FIG. 11 are diagrams showing an example of power control in a one-time puff action according to the first embodiment. FIG. 10 and FIG. 11 illustrate a case in which the user must end a puff action series, in principle, when the number of times of the puff action reaches eight times (predetermined number of times).

Here, a case in which the power source output supplied to the heat source 80 is controlled depending on the voltage applied to the heat source 80 will be illustrated. Therefore, in the first embodiment, it may be assumed that the power source output is synonymous with voltage. Further, FIG. 10 shows a behavior of the voltage that is applied to the heat source 80 in the standard mode, and FIG. 11 shows a behavior of the voltage that is applied to the heat source 80 in the shortened mode.

As shown in FIG. 10, in the standard mode, the standard voltage is applied to the heat source 80 for the duration until a first time period T1 elapses. A voltage smaller than the standard voltage is applied to the heat source 80 for the duration after the first time period T1 has elapsed.

Here, a case is illustrated in which the first time period T1 is the same as the end timing of the standard required time duration. However, as described above, the first time period T1 is not limited thereto.

As shown in FIG. 11, in the shortened mode, a first voltage that is larger than the standard voltage is applied to the heat source 80 for the duration until a second time period T2 elapses. A second voltage that is smaller than the first voltage is applied to the heat source 80 for the duration until a third time period T3 after the second time period T2 elapses. A voltage smaller than the second voltage is applied to the heat source 80 for the duration after the third time period T3 has elapsed.

Here, a case is illustrated in which the second time period is shorter than the start timing of the standard required time duration. A case is illustrated in which the third time period is same as the end timing of the standard required time duration. A case is illustrated in which the second voltage is smaller than the standard voltage. However, as described above, the second time period T2, the third time period T3, and the second voltage are not limited thereto.

It is noted that a change in the required time of a one-time puff action is expected when the standard mode or the shortened mode has been set. Even in such a case, it must be noted that the voltage becomes zero at the same timing of the end of the puff action by tracing the profile of the voltage shown in FIG. 10 or FIG. 11. In other words, it must be noted that complex control such as continuous control of the amount of supply of the power source output on the basis of the air flow (inhalation rate) is unnecessary during the time when the power source output is being supplied to the heat source 80, since it may be favorable to control the power source output to the heat source according to the predetermined action mode.

(Operation and Effect)

In the first embodiment, the control circuit 50 (puff detection portion 51) detects the start or the end of the puff duration, when an inclination configured by two or more output values that are output from the sensor 20 has a predetermined sign (for example, negative), and an absolute value of the inclination having the predetermined sign is larger than a predetermined value. Therefore, it is possible to reduce the possibility of erroneously detecting, as the start of the puff duration, an output result of the sensor (for example, the pressure change at a high place, the vibration of human voice, etc.) that is originally not intended as the start of the puff duration, and the possibility of deterioration in the following capability of the power source output to the heat source 80, and thus, it is possible to enhance the detection accuracy of the puff duration. That is, it is possible to achieve both the improvement in the detection accuracy of the puff duration and the improvement in the following capability of the power source output.

In the first embodiment, when detecting the start or the end of the puff duration, the sensor 20 is used, configured to output electric capacitance of a capacitor that changes depending on the puff action of the user. As shown in FIG. 5, by focusing on a point that the pressure change within a housing configured to form an air flow path is specific in an early period and an ending period of inhaling action, then using a sensor capable of outputting such a pressure change, a response of detecting the puff duration is improved.

In the first embodiment, the sampling cycle (Δta or Δtc) in which the output value that is output from the sensor 20 is monitored outside the puff duration is shorter than the sampling cycle (Δtb) in which the output value that is output from the sensor 20 is monitored within the puff duration. Thus, it is possible to reduce electric power necessary for monitoring the output value that is output from the sensor 20 in the puff duration while securing the following capability of the power source output with respect to the heat source 80 by maintaining the accuracy of detecting the start of the puff duration. It must be noted that there is no problem in that the accuracy of detecting the end of the puff duration is lower than the accuracy of detecting the start of the puff duration.

In the first embodiment, the control circuit 50 (puff detection portion 51) detects the start of the puff duration, when, for consecutive m times (m is an integer value of 2 or more) of S(n), a condition is satisfied before the detection of the start of the puff duration in which all S(n)s are a negative value, and the absolute value of all S(n)s is larger than the first value. On the other hand, the control circuit 50 (puff detection portion 51) detects the end of the puff duration, when, for consecutive m times of S(n), a condition is satisfied after the detection of the start of the puff duration in which S(n) is a negative value, and the absolute value of S(n) is larger than the first value. Thus, by using consecutive m times of S(n) when detecting the start or the end of the puff duration, it is possible to improve the detection accuracy of the puff duration.

In the first embodiment, in the non-puffing state in which aerosol is not inhaled, the light-emitting element controller 52 controls the light-emitting element 40 according to the second light-emitting mode that is different from the first light-emitting mode. As a result, even in the non-puffing state, it is possible to make the user understand whether or not the non-burning type flavor inhaler 100 is in a usable state. Further, since the light-emitting mode in the puffing state is different from the light-emitting mode in the non-puffing state, it is possible to realize a sense of use that resembles the sense of use of a regular cigarette in which aerosol is generated in association with burning.

In the first embodiment, the second light-emitting mode changes in accordance with the number of times of the puff action of inhaling aerosol. As a result, in the non-puffing state in which the emitted light of the light-emitting element 40 is easily visually recognized, the user is capable of easily understanding the progress status of puffing by the change in the second light-emitting mode.

In the first embodiment, the heat source controller 53 gradually increases the power source output to the heat source 80 from the standard power source output in association with an increase in the number of times of the puff action of inhaling the aerosol. As a result, it is possible to bring the amount of supply of the aerosol closer to the regular cigarette in which aerosol is generated in association with burning, and it is possible to realize a sense of use that resembles that of a regular cigarette.

In the first embodiment, the heat source controller 53 arranges the tobacco source 131 at the mouthpiece side from the holder 60 (aerosol source), and gradually increases the power source output to the heat source 80 from the standard power source output with an increase in the number of times of the puff action of inhaling the aerosol. As a result, it is possible to maintain an amount of supply of an alkaloid at a level close to an amount of supply of an alkaloid in an initial puff.

Specifically, with a configuration in which an alkaloid is contained in the aerosol source, such as an existing electric cigarette, the proportion of the alkaloid contained in the aerosol is constant. Therefore, in order to bring the amount of supply of the aerosol closer to that of the regular cigarette by using such a configuration, if the power source output to the heat source 80 is increased gradually from the standard power source output, then the amount of supply of the alkaloid increases in proportion with the amount of supply of the aerosol.

In contrast, in the first embodiment, a configuration is adopted in which the tobacco source 131 is arranged at the mouthpiece side from the holder 60 (aerosol source). The present inventors, etc. discovered a phenomenon by which the proportion of the alkaloid contained in the aerosol reduces with an increase in the number of times of puffing. As a result, in order to bring the amount of supply of the aerosol closer to that of the regular cigarette, if the power source output to the heat source 80 is increased gradually from the standard power source output, then the amount of supply of the alkaloid is maintained at a level close to the amount of supply of the alkaloid in the first puff.

Thus, in the first embodiment, in the configuration in which the tobacco source 131 is arranged at the mouthpiece side from the holder 60 (aerosol source), the heat source controller 53 gradually increases the power source output to the heat source 80 from the standard power source output with an increase in the number of times of the puff action of inhaling the aerosol. As a result, it is possible to maintain the amount of supply of the alkaloid at a level close to the amount of supply of the alkaloid in the first puff while bringing the amount of supply of the aerosol closer to that of the regular cigarette.

In the first embodiment, the heat source controller 53 controls a first mode in which a first standard power source output is used as the standard power source output, and a second mode in which a second standard power source output that is greater than the first standard power source output is used as the standard power source output. As a result, it is possible for the user to select an aerosol amount in accordance with a preference of the user, with a single non-burning type flavor inhaler 100.

In the first embodiment, even in the case of a user for whom the required time of a one-time puff action is shorter than the standard required time, it is possible to improve the level of satisfaction of such a user by raising the temperature of the heat source faster than the standard mode by introducing the shortened mode. Regardless of the action mode, since the power source output to the heat source is reduced for the duration after the first time period or the third time period has elapsed, inhaling of decomposed substances is prevented, and a drop in flavor is also prevented.

In the first embodiment, the predetermined action mode (standard mode and shortened mode) is provided, and thus it may be favorable to control the power source output to the heat source according to the predetermined action mode. As a result, during the period when power source output is being supplied to the heat source 80, complex control such as continuous control of the amount of supply of the power source output on the basis of the air flow (inhalation rate) is unnecessary. In other words, it is possible to realize a drop in the flavor, and an improvement in the level of satisfaction of the user, with a simple configuration.

[First Modification]

A first modification of the first embodiment will be described, below. Description proceeds with a particular focus on a difference from the first embodiment, below.

Specifically, in the above-described first embodiment, the heat source controller 53 controls the power source output to the heat source 80 from the power source 10 by controlling the voltage applied to the heat source 80 from the power source 10. In particular, the heat source controller 53 gradually increases the power source output (voltage) to the heat source 80 from the standard power source output (standard voltage) with an increase in the number of times of the puff action of inhaling the aerosol (see FIG. 9).

In contrast, in the first modification, the heat source controller 53 controls the voltage that is applied to the heat source 80 from the power source 10 by pulse control, and controls the power source output to the heat source 80 from the power source 10 by controlling the pulse width (Duty ratio) at which the voltage is applied to the heat source 80. In particular, the heat source controller 53 gradually shortens the pulse width at which the voltage is applied to the heat source 80 from the standard pulse width with an increase in the number of times of the puff action of inhaling the aerosol (see FIG. 12).

It is noted that following the example shown in FIG. 9, FIG. 12 illustrates a case in which the power source output is increased between the puffing state #4 and the puffing state #5. Although the puffing states other than the puffing state #4 and the puffing state #5 are omitted in FIG. 15, it is a matter of course that a similar effect as in the example shown in FIG. 9 is obtained by controlling the pulse width (Duty ratio).

[Second Modification]

A second modification of the first embodiment will be described, below. Description proceeds with a particular focus on a difference from the first embodiment, below.

Specifically, in the above-described first embodiment, the heat source controller 53 controls the power source output to the heat source 80 from the power source 10 by controlling the voltage applied to the heat source 80 from the power source 10. In particular, the heat source controller 53 gradually increases the power source output (voltage) to the heat source 80 from the standard power source output (standard voltage) with an increase in the number of times of the puff action of inhaling the aerosol (see FIG. 9).

In contrast, in the second modification, the heat source controller 53 controls the power source output to the heat source 80 from the power source 10 by controlling the time interval during which the voltage is applied to the heat source 80. In particular, the heat source controller 53 gradually extends the time interval during which the voltage is applied to the heat source 80 from the standard time interval with an increase in the number of times of the puff action of inhaling the aerosol (see FIG. 13).

In the second modification, the standard time interval implies the maximum time for which the application of voltage to the heat source 80 is continued when the user continues the puff action. Therefore, if the time period during which the user continues the puff action exceeds the standard time interval, the application of voltage to the heat source 80 stops. It is noted that even if the application of voltage stops, the first light-emitting mode of the light-emitting element 40 is maintained during the time the puff action of the user continues. As a result, since the total power source output supplied to the heat source 80 in a one-time puff action changes, the similar effect as in the example shown in FIG. 9 is obtained.

It is noted that when the standard mode and the shortened mode described in the first embodiment are introduced, the first time period, the second time period, and the third time period may be adjusted (extended) with an increase in the number of times of the puff action of inhaling the aerosol.

[Third Modification]

A third modification of the first embodiment will be described, below. Description proceeds with a particular focus on a difference from the first embodiment, below.

Specifically, in the above-described first embodiment, as described in detail in the above-described first embodiment, the control circuit 50 (puff detection portion 51) detects the start of the puff duration, when, for consecutive m times (m is an integer value of 2 or more) of S(n), a condition is satisfied before the detection of the start of the puff duration in which all S(n)s are a negative value, and the absolute value of all S(n)s is larger than the first value. Thus, even in a case in which the user performs blowing from the mouthpiece of the non-burning type flavor inhaler 100 toward the inside of the non-burning type flavor inhaler 100, it is possible to reduce the possibility of erroneously detecting such an action as the start of the puff duration.

In contrast, a third modification further includes a means by which the blowing is detected when the user performs blowing, and the user is notified about the detection of blowing.

Specifically, the control circuit 50 (puff detection portion 51) detects the start of blowing, when, for consecutive m times of S(n), a condition is satisfied before the detection of the start of the puff duration in which all S(n)s are a positive value, and the absolute value of all S(n)s is larger than the first value. That is, in the third modification, the detection of blowing is performed by using the fact that the positive and negative signs are reversed in a sensor output pattern that is obtained when blowing is performed as compared to a pattern that is obtained when the puff action is performed.

When blowing is detected in the puff detection portion 51, the light-emitting controller 52 controls the light-emitting element 40 by a light-emitting mode that is different from the above-described first light-emitting mode and second light-emitting mode. That is, in the third modification, by controlling the light-emitting element 40 by a light-emitting mode that is different from the above-described first light-emitting mode and second light-emitting mode, the user is notified about the detection of blowing.

It is noted that, similarly to the case in the first embodiment, it is but natural that when blowing is detected in the puff detection portion 51, the heat source controller 53 does not perform the supply of power source output to the heat source 80 from the power source 10.

[Other Embodiments]

The present invention is described through the above-described embodiments, but it should not be understood that this invention is limited by the statements and the drawings constituting a part of this disclosure. From this disclosure, various alternative embodiments, examples, and operational technologies will become apparent to those skilled in the art.

In the embodiments, the tobacco source 131 is illustrated as the flavor source. However, the embodiment is not limited thereto. The flavor source may not necessarily include a tobacco raw material. In addition, the non-burning type flavor inhaler 100 may not have a flavor source, and an inhaling flavor component may be added to the aerosol source.

In the embodiments, a case is illustrated in which the non-burning type flavor inhaler 100 has the capsule unit 130. However, the embodiment is not limited thereto. For example, the non-burning type flavor inhaler 100 may have a cartridge containing the flavor source.

In the embodiments, a case is illustrated in which the puff detection portion 51 detects the start or the end of the puff duration, when the inclination configured by two or more output values that are output from the sensor 20 has a negative sign, and the absolute value of the inclination having a negative sign is larger than a predetermined value. However, the embodiment is not limited thereto. Specifically, the puff detection portion 51 may detect the start or the end of the puff duration, when the inclination configured by two or more output values that are output from the sensor 20 has a positive sign, and the absolute value of the inclination having a positive sign is larger than a predetermined value. In such a case, the expression "negative" in the embodiments may be replaced by "positive". Consideration must be given to the fact that which one of "positive" and "negative"

needs to be applied depends on the type of the sensor 20, etc., that is, depends on an output pattern of the sensor 20 with respect to the puff action of the user.

In the embodiment, a case is described in which the sensor 20 is a capacitor microphone sensor. However, the type of sensor 20 is not limited thereto. The sensor 20 may be configured by, for example, a piezoelectric element detecting the electric capacitance of the capacitor changed depending on the puff action of the user.

Although not particularly specified in the embodiments, the push button 30 configures a switch member for starting and stopping the supply of electric power to the control circuit 50 and the sensor 20 from the power source 10. Since the supply of power to the sensor 20 is stopped by pushing the push button 30, it is possible to realize a reduction in the consumption of electric power.

Although not particularly specified in the embodiments, when the output value that is monitored at the sampling cycle Δta does not change over a predetermined time period (for example, 200 msec. to 500 msec.) before the start of the puff duration is detected, the sensor 20 may be turned OFF. As a result, it is possible to realize energy-saving. Further, in such a case, it is preferable to turn ON the sensor 20 when a predetermined time period (for example, 50 msec.) has elapsed since turning OFF the sensor 20. As a result, it is possible to secure the following capability of the power source output with respect to the heat source 80 while saving energy. It must be noted that when the output value that is monitored at the sampling cycle Δta changes, the sensor 20 is turned ON continuously. It is noted that, as a behavior different from the ON/OFF behavior of such a sensor 20, the sensor 20 may be repeatedly turned ON/OFF in synchronization with the sampling cycle (Δt) and the calculation cycle of S(n).

In the embodiments, although not particularly mentioned, since the tobacco source 131 is held within the capsule unit 130, the pH of the tobacco raw material contained in the tobacco source 131 may be changed for each capsule unit 130. In such a case, depending on the type of the capsule unit 130, the gradient of the power source output to the heat source 80 may be changed with an increase in the number of times of the puff action.

In the embodiments, although not particularly mentioned, the number of times of the puff action may be corrected by a value (the amount of generation of the aerosol) defined by the power source output to the heat source 80 in a one-time puff action. Specifically, if the amount of aerosol generated in a one-time puff action is smaller than the default value, the number of times of the puff action may be accumulated by adding a value obtained by multiplying a predetermined coefficient α (α<1) once. On the other hand, if the amount of aerosol generated in a one-time puff action is greater than the default value, the number of times of the puff action may be accumulated by adding a value obtained by multiplying a predetermined coefficient β (β>1) once. That is, the number of times of the puff action need not necessarily be an integer.

In the embodiments, although not particularly mentioned, in the power control of the puff action series, the timing of increasing the power source output to the heat source 80 is preferably synchronized with the timing of changing the second light-emitting mode. For example, as shown in FIG. 8 and FIG. 9, when the power source output (voltage) to the heat source 80 is increased between the puffing state #4 and the puffing state #5, the second light-emitting mode preferably changes between the puffing state #4 and the puffing state #5.

In the embodiments, although not particularly specified, as shown in FIG. 10 and FIG. 11, a voltage that is smaller than the standard voltage is applied to the heat source 80 for the duration after the first time period T1 or the third time period T3 has elapsed; however, the first light-emitting mode preferably continues even for such a duration.

In the embodiments, the first mode (Low mode shown in FIG. 8) in which the first standard power source output is used as the standard power source output, and the second mode (High mode shown in FIG. 9) in which the second standard power source output that is greater than the first standard power source output is used as the standard power source output, are provided. In such a case, the light-emitting mode of the first mode may be different from the light-emitting mode of the second mode. That is, each of the first light-emitting mode, the second light-emitting mode, and the end light-emitting mode of the first mode may be different from the first light-emitting mode, the second light-emitting mode, and the end light-emitting mode of the second mode.

Although not particularly mentioned in the embodiments, a program may be provided, configured to cause a computer to execute each process performed by the non-burning type flavor inhaler 100. Further, the program may be recorded on a computer-readable medium. By using the computer-readable medium, it is possible to install the program in a computer. Here, the computer-readable medium in which the program is recorded thereon may include a non-transitory recording medium. The non-transitory recording medium is not particularly limited; the non-transitory recording medium may include a recording medium such as a CD-ROM or a DVD-ROM, for example.

Alternatively, a chip may be provided which is configured by: a memory in which a program for executing each process performed by the non-burning type flavor inhaler 100 is stored; and a processor configured to execute the program stored in the memory.

It is noted that the entire content of Japanese Patent Application No. 2014-095164 (filed on May 2, 2014) is incorporated in the subject application by reference.

INDUSTRIAL APPLICABILITY

According to the embodiment, it is possible to provide a non-burning type flavor inhaler capable of enhancing the detection accuracy of the puff duration as well as improving the response of the detection of the puff duration.

The invention claimed is:
1. A non-burning type flavor inhaler, comprising:
   a housing having an airflow path that continues from an inlet to an outlet;
   an atomizer configured to atomize an aerosol source without burning;
   a sensor including a capacitor, the sensor outputting a value indicating electric capacitance of the capacitor, the electric capacitance changed depending on a puff action of a user; and
   a controller configured to detect a start or an end of a puff duration on the basis of an output value that is output from the sensor,
   wherein the controller comprises a puff detection portion configured to detect the start or the end of the puff duration when an inclination formed by two or more of the output values has a predetermined sign and when an absolute value of the inclination having the predetermined sign is larger than a predetermined value.

2. The non-burning type flavor inhaler according to claim 1, wherein
   a cycle for monitoring the output value output from the sensor before detecting the start of the puff duration is shorter than a cycle for monitoring the output value output from the sensor after detecting the start of the puff duration, and
   a cycle for monitoring the output value output from the sensor after detecting the end of the puff duration is shorter than a cycle for monitoring the output value output from the sensor before detecting the end of the puff duration.

3. The non-burning type flavor inhaler according to claim 1, wherein
   $\Delta t$ represents a cycle for monitoring the output value output from the sensor,
   $D(n)$ represents the output value output from the sensor at a time $t(n)$,
   $\alpha(n)$ represents a positive integer,
   $S(n)$ represents an inclination formed by the output value output from the sensor at a time $t(n)$,
   the puff detection portion calculates the inclination formed by the output value output from the sensor based on $S(n)=\{D(n)-D(n-\alpha(n)\times\Delta t)\}/(\alpha(n)\times\Delta t)$,
   the puff detection portion detects the start or the end of the puff duration when a condition in that $S(n)$ is a value of the predetermined sign and an absolute value of $S(n)$ is larger than a first value is satisfied for consecutive m times (m is an integer of 2 or more) of $S(n)$.

4. The non-burning type flavor inhaler according to claim 3, wherein
   a sampling cycle of the output value that is referenced upon detecting the start or the end of the puff duration is longer than a predetermined time, and
   the predetermined time is longer than ½ of an average value of wavelength of the output value varied in the puff duration.

5. The non-burning type flavor inhaler according to claim 3, wherein
   the puff detection portion detects the start or the end of the puff duration when a condition that $S(n)$ is a value of the predetermined sign and an absolute value of $S(n)$ is smaller than a second value is satisfied for one time of the consecutive m times of $S(n)$, and
   the second value is an average value of an absolute value of the inclination formed by the output value varied in the puff duration.

6. The non-burning type flavor inhaler according to claim 1, wherein the sensor is a capacitor microphone sensor.

7. The non-burning type flavor inhaler according to claim 1, comprising a switch member used for starting and stopping a supply of power source output to the controller and the sensor.

* * * * *